(12) United States Patent
Stulen et al.

(10) Patent No.: US 10,238,416 B2
(45) Date of Patent: Mar. 26, 2019

(54) ULTRASONIC DEVICE FOR CUTTING AND COAGULATING

(71) Applicant: Ethicon Endo-Surgery, Inc., Cincinnati, OH (US)

(72) Inventors: Foster B. Stulen, Mason, OH (US); John B. Schulte, West Chester, OH (US); Jeffrey L. Aldridge, Lebanon, OH (US); Jeffery T. Kirk, Liberty Township, OH (US); Randal T. Byrum, South Lebanon, OH (US); Douglas J. Turner, Cincinnati, OH (US); John M. Sarley, Mason, OH (US); David A. Witt, Maineville, OH (US); William A. Olson, Lebanon, OH (US); Kyle P. Moore, Woodstock, GA (US)

(73) Assignee: Ethicon LLC, Guaynabo, PR (US)

( * ) Notice: Subject to any disclaimer, the term of this patent is extended or adjusted under 35 U.S.C. 154(b) by 968 days.

(21) Appl. No.: 13/868,336

(22) Filed: Apr. 23, 2013

(65) Prior Publication Data

US 2013/0289592 A1 Oct. 31, 2013

Related U.S. Application Data

(60) Provisional application No. 61/640,227, filed on Apr. 30, 2012, provisional application No. 61/722,986, filed on Nov. 6, 2012.

(51) Int. Cl.
*A61B 17/32* (2006.01)
*A61B 17/00* (2006.01)
*A61B 90/00* (2016.01)

(52) U.S. Cl.
CPC ........... *A61B 17/320092* (2013.01); *A61B 17/320068* (2013.01); *A61B 2017/00017* (2013.01);
(Continued)

(58) Field of Classification Search
CPC .... A61B 17/320068; A61B 17/320092; A61B 2017/320072; A61B 2017/320088; A61B 2017/320078
(Continued)

(56) References Cited

U.S. PATENT DOCUMENTS 5,322,055 A * 6/1994 Davison ........... A61B 17/32006
601/2
5,873,873 A * 2/1999 Smith ............ A61B 17/320092
606/1
(Continued)

FOREIGN PATENT DOCUMENTS

CN 101511286 A 8/2009
CN 101600393 A 12/2009
(Continued)

OTHER PUBLICATIONS

International Search Report and Written Opinion for Application No. PCT/US2013/038396 dated Jul. 9, 2013.
(Continued)

*Primary Examiner* — Ryan J Severson
*Assistant Examiner* — Christian Knauss
(74) *Attorney, Agent, or Firm* — Frost Brown Todd LLC

(57) ABSTRACT

A surgical apparatus comprises a body, an ultrasonic transducer, a shaft, and an end effector. The ultrasonic transducer is operable to convert electrical power into ultrasonic vibrations. The shaft couples the end effector and the body together. The end effector comprises an ultrasonic blade in acoustic communication with the ultrasonic transducer. The ultrasonic blade includes a recess region having a plurality of recesses. The recess region is tapered such that the cross-sectional area of the recess region decreases along the length of the recess region. The ultrasonic blade is also curved such that a central longitudinal axis of the ultrasonic
(Continued)

blade extends along a curved path. A reference circuit is used to account for voltage drops of unknown values during operation of the surgical apparatus.

20 Claims, 23 Drawing Sheets

(52) U.S. Cl.
CPC ............. *A61B 2017/00725* (2013.01); *A61B 2017/320072* (2013.01); *A61B 2017/320088* (2013.01); *A61B 2090/0814* (2016.02)

(58) Field of Classification Search
USPC .......................................................... 361/94
See application file for complete search history.

(56) References Cited

U.S. PATENT DOCUMENTS

| | | | |
|---|---|---|---|
| 5,980,510 A | 11/1999 | Tsonton et al. | |
| 6,066,979 A * | 5/2000 | Adams | G05F 1/46 327/538 |
| 6,309,400 B2 | 10/2001 | Beaupre | |
| 6,325,811 B1 * | 12/2001 | Messerly | A61B 17/32009 606/169 |
| 6,666,875 B1 | 12/2003 | Sakurai et al. | |
| 6,773,444 B2 | 8/2004 | Messerly | |
| 6,783,524 B2 | 8/2004 | Anderson et al. | |
| 8,461,744 B2 | 6/2013 | Wiener et al. | |
| 8,814,895 B2 | 8/2014 | Messerly | |
| 9,402,682 B2 | 8/2016 | Worrell et al. | |
| 2001/0027325 A1 * | 10/2001 | Beaupre | A61B 17/320068 606/169 |
| 2006/0079874 A1 | 4/2006 | Faller et al. | |
| 2007/0191713 A1 * | 8/2007 | Eichmann | A61B 17/1606 600/471 |
| 2007/0282333 A1 | 12/2007 | Fortson et al. | |
| 2008/0146921 A1 * | 6/2008 | Novak | A61B 17/320068 600/437 |
| 2008/0200940 A1 | 8/2008 | Eichmann et al. | |
| 2009/0105750 A1 | 4/2009 | Price et al. | |
| 2010/0069940 A1 * | 3/2010 | Miller | A61B 17/320068 606/169 |
| 2010/0204721 A1 * | 8/2010 | Young | A61B 17/320068 606/169 |
| 2011/0087212 A1 * | 4/2011 | Aldridge | A61B 17/320092 606/34 |
| 2012/0029546 A1 | 2/2012 | Robertson | |
| 2012/0078278 A1 * | 3/2012 | Bales, Jr. | A61B 17/320092 606/169 |
| 2012/0112687 A1 | 5/2012 | Houser et al. | |
| 2012/0116265 A1 | 5/2012 | Houser et al. | |

FOREIGN PATENT DOCUMENTS

| | | |
|---|---|---|
| CN | 102149338 A | 8/2011 |
| EP | 0908151 | 4/1999 |
| RU | 2433807 C2 | 11/2011 |
| WO | WO 2007/047380 | 4/2007 |

OTHER PUBLICATIONS

U.S. Appl. No. 13/538,588, filed Jun. 29, 2012.
U.S. Appl. No. 13/657,553, filed Oct. 22, 2012.
U.S. Appl. No. 61/410,603, filed Nov. 5, 2010.
U.S. Appl. No. 61/640,227, filed Apr. 30, 2012.
U.S. Appl. No. 61/722,986, filed Nov. 6, 2012.
Australian Office Action, Patent Examination Report No. 1, dated Oct. 11, 2016 for Application No. AU 2013256686, 4 pgs.
Chinese Office Action, Notification of the First Office Action, dated Apr. 29, 2016 for Application No. 201380022660.3, 11 pgs.
Chinese Search Report dated Apr. 17, 2016 for Application No. CN 201380022660.3, 3 pgs.
Japanese Office Action, Notification of Reasons for Refusal, dated Apr. 4, 2017 for Application No. 2015-510347, 6 pgs.
Australian Office Action, Examination report No. 1 for standard patent application, dated Dec. 8, 2017 for Application No. AU 2017245348, 3 pgs.
Japanese Office Action, Notification of Reasons for Refusal, dated Jan. 9, 2018 for Application No. JP 2015-510347, 3 pgs.
Mexican Office Action, $2^{nd}$ Substantive Examination Requirement IPL PCT, dated Nov. 22, 2017 for Application No. MX/a/2014/013199, 4 pgs.
Russian Office Action, Official Action and Search Report, dated Aug. 1, 2017 for Application No. RU 2014148146/14, 6 pgs.

* cited by examiner

ULTRASONIC DEVICE FOR CUTTING AND COAGULATING

PRIORITY

This application claims priority to U.S. Provisional Pat. App. No. 61/640,227, entitled "Ultrasonic Device for Cutting and Coagulating," filed Apr. 30, 2012, the disclosure of which is incorporated by reference herein.

This application also claims priority to U.S. Provisional Pat. App. No. 61/722,986, entitled "Ultrasonic Device for Cutting and Coagulating," filed Nov. 6, 2012, the disclosure of which is incorporated by reference herein.

BACKGROUND

A variety of surgical instruments include an end effector having a blade element that vibrates at ultrasonic frequencies to cut and/or seal tissue (e.g., by denaturing proteins in tissue cells). These instruments include piezoelectric elements that convert electrical power into ultrasonic vibrations, which are communicated along an acoustic waveguide to the blade element. The precision of cutting and coagulation may be controlled by the surgeon's technique and adjusting the power level, blade edge, tissue traction and blade pressure.

Examples of ultrasonic surgical instruments include the HARMONIC ACE®Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; and U.S. Pat. No. 6,783,524, entitled "Robotic Surgical Tool with Ultrasound Cauterizing and Cutting Instrument," issued Aug. 31, 2004, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; U.S. Pub. No. 2009/0105750, entitled "Ergonomic Surgical Instruments," published Apr. 23, 2009, issued as U.S. Pat. No. 8,623,027 on Jan. 7, 2014, the disclosure of which is incorporated by reference herein; U.S. Pub. No. 2010/0069940, entitled "Ultrasonic Device for Fingertip Control," published Mar. 18, 2010, issued as U.S. Pat. No. 9,023,071 on May 5, 2015, the disclosure of which is incorporated by reference herein; and U.S. Pub. No. 2011/0015660, entitled "Rotating Transducer Mount for Ultrasonic Surgical Instruments," published Jan. 20, 2011, issued as U.S. Pat. No. 8,461,744 on Jun. 11, 2013, the disclosure of which is incorporated by reference herein; U.S. Pub. No. 2012/0029546, entitled "Ultrasonic Surgical Instrument Blades," published Feb. 2, 2012, issued as U.S. Pat. No. 8,591,536 on Nov. 26, 2013, the disclosure of which is incorporated by reference herein; U.S. patent application Ser. No. 13/538,588, filed Jun. 29, 2012, issued as U.S. Pat. No. 9,393,037 on Jul. 19, 2016, entitled "Surgical Instruments with Articulating Shafts," the disclosure of which is incorporated by reference herein; and U.S. patent application Ser. No. 13/657,553, filed Oct. 22, 2012, issued as U.S. Pat. No. 9,095,367 on Aug. 4, 2015, entitled "Flexible Harmonic Waveguides/Blades for Surgical Instruments," the disclosure of which is incorporated by reference herein.

Additionally, some of the foregoing surgical instruments may include a cordless transducer such as that disclosed in U.S. Pub. No. 2012/0112687, entitled "Recharge System for Medical Devices," published May 10, 2012, issued as U.S. Pat. No. 9,381,058 on Jun. 5, 2016, the disclosure of which is incorporated by reference herein; U.S. Pub. No. 2012/0116265, entitled "Surgical Instrument with Charging Devices," published May 10, 2012, now abandoned, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
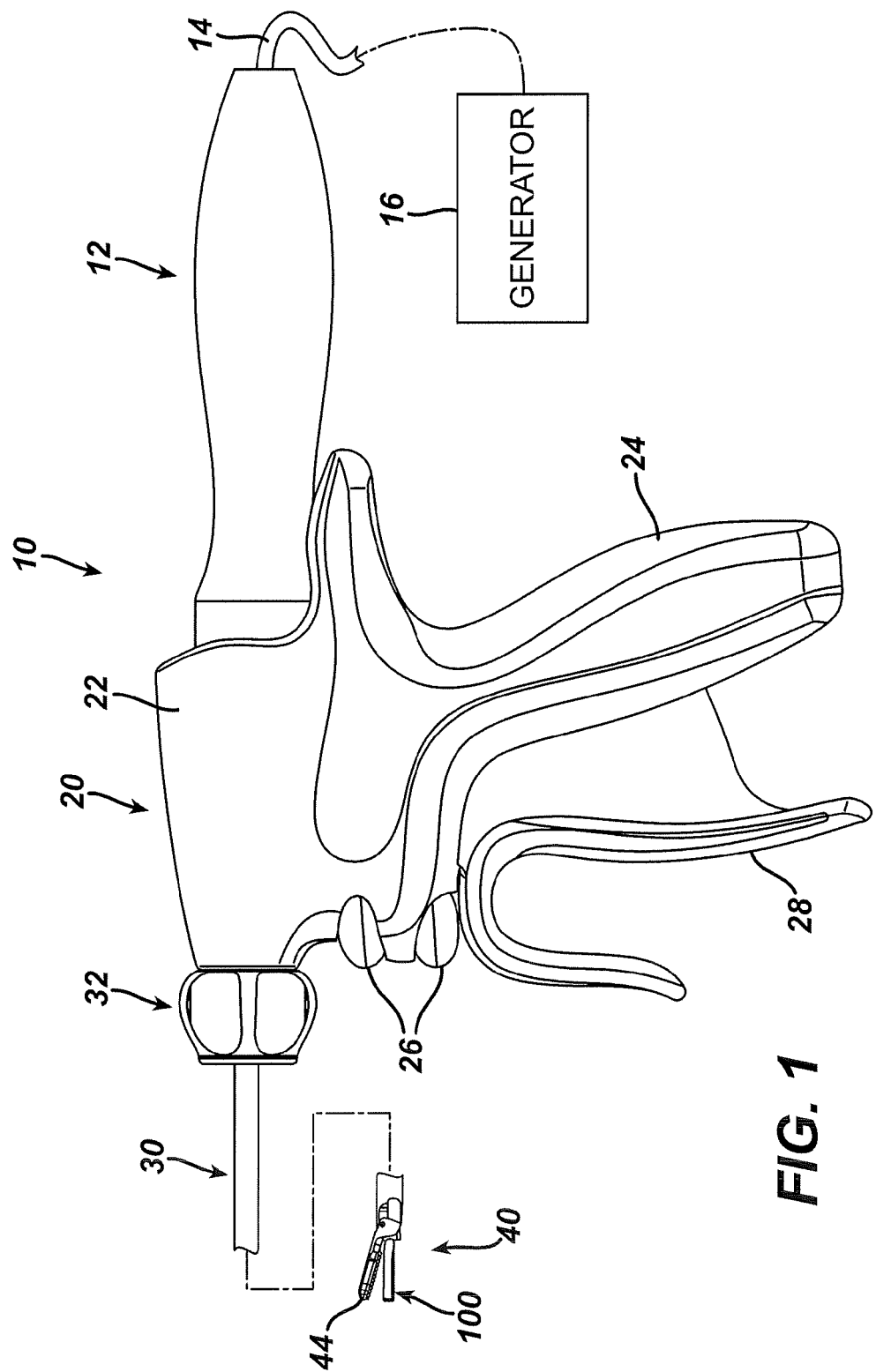
FIG. 1 depicts a side elevational view of an exemplary ultrasonic surgical instrument.
Figure 2:
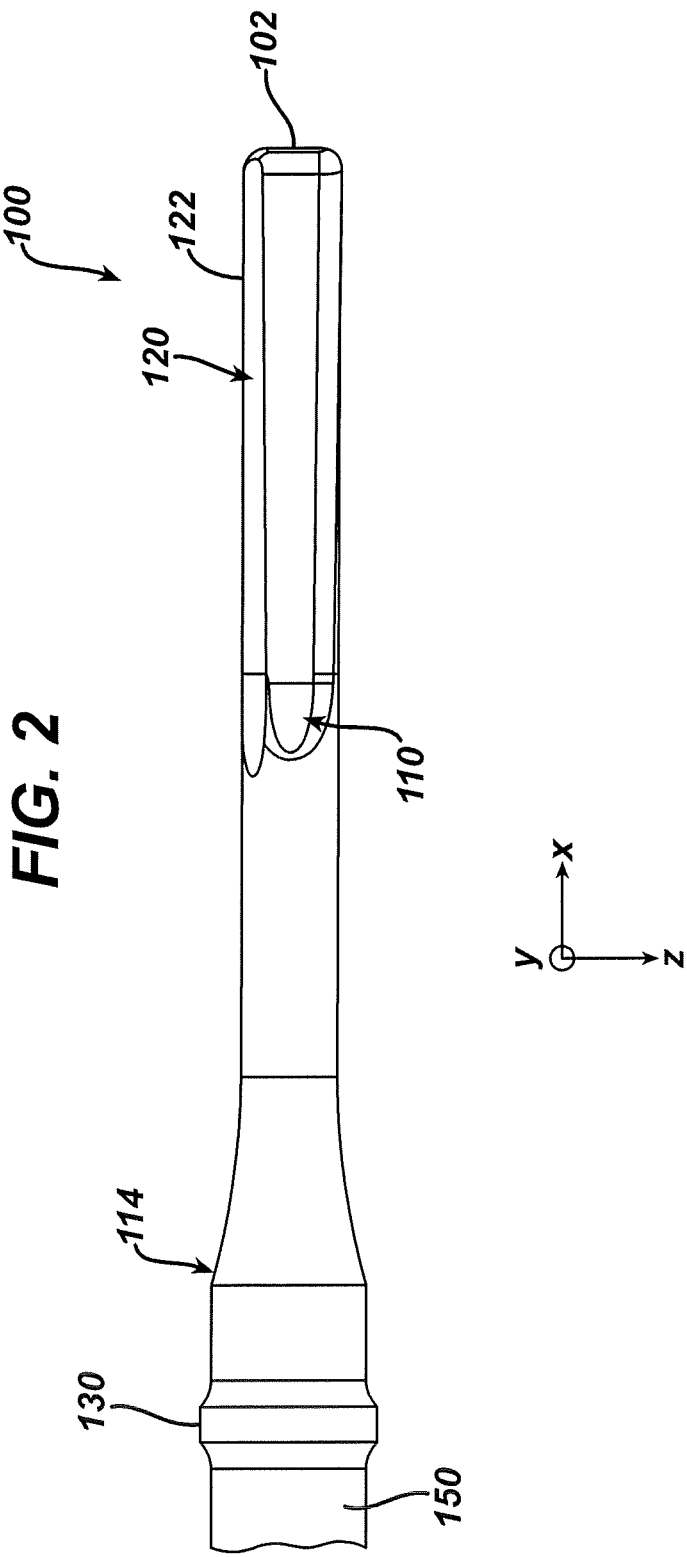
FIG. 2 depicts a left elevational view of an ultrasonic blade of the surgical instrument of FIG. 1.
Figure 3:
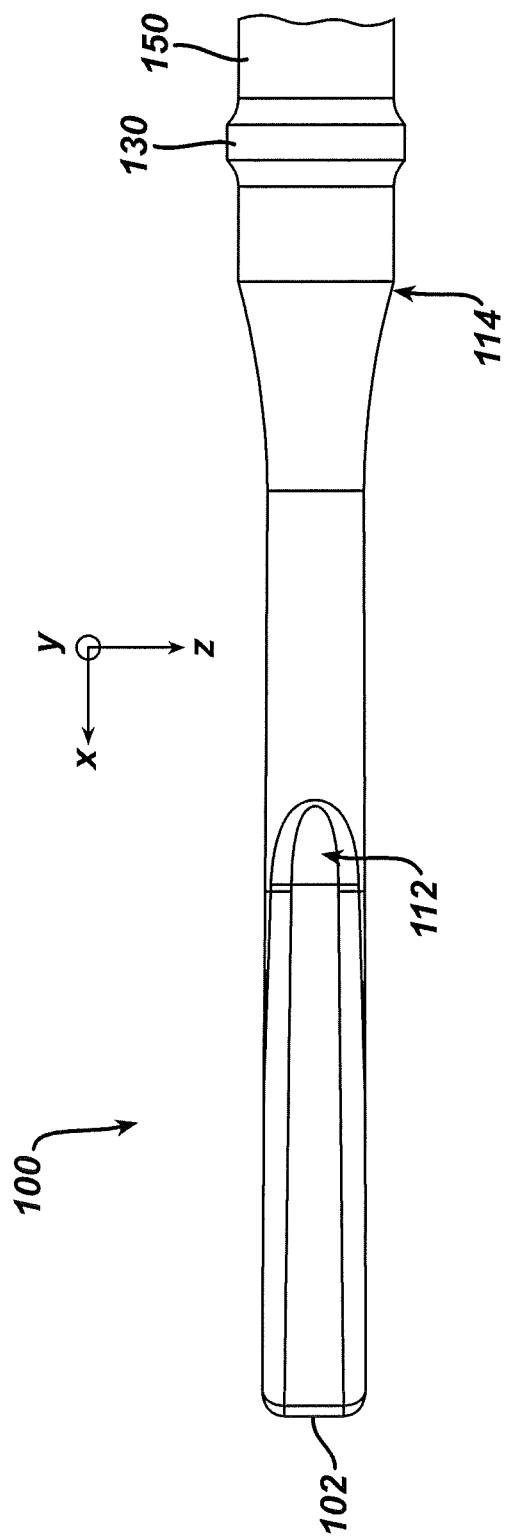
FIG. 3 depicts a right elevational view of the ultrasonic blade of FIG. 2.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument.

I. Exemplary Ultrasonic Surgical Instrument

FIG. 1 illustrates an exemplary ultrasonic surgical instrument (10). At least part of instrument (10) may be constructed and operable in accordance with at least some of the teachings of U.S. Pat. Nos. 5,322,055; 5,873,873; 5,980, 510; 6,325,811; 6,773,444; 6,783,524; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940, now abandoned; U.S. Pub. No. 2009/0105750, issued as U.S. Pat. No. 8,623,027 on Jan. 7, 2014; U.S. Pub. No. 2010/0069940, issued as U.S. Pat. No. 9,012,071 on May. 5, 2015; U.S. Pub. No. 2011/0015660, issued as U.S. Pat. No. 8,461,744 on Jun. 11, 2013; U.S. Pub. No. 2012/0112687, issued as U.S. Pat. No. 9,381, 058 on Jun. 5, 2016; U.S. Pub. No. 2012/0116265, now abandoned; U.S. patent application Ser. No. 13/538,588, issued as U.S. Pat. No. 9,393,037 on Jul. 19, 2016; U.S. patent application Ser. No. 13/657,553, issued as U.S. Pat. No. 9,095,367 on Aug. 4, 2015; and/or U.S. Pat. App. No. 61/410,603. The disclosures of each of the foregoing patents, publications, and applications are incorporated by reference herein. As described therein and as will be described in greater detail below, instrument (10) is operable to cut tissue and seal or weld tissue (e.g., a blood vessel, etc.) substantially simultaneously. It should also be understood that instrument (10) may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, instrument (10) may have various structural and functional similarities with the devices taught in any of the other references that are cited and incorporated by reference herein.

To the extent that there is some degree of overlap between the teachings of the references cited herein, the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades, and the following teachings relating to instrument (10), there is no intent for any of the description herein to be presumed as admitted prior art. Several teachings herein will in fact go beyond the scope of the teachings of the references cited herein and the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades.

Instrument (10) of the present example comprises a handle assembly (20), a shaft assembly (30), and an end effector (40). Handle assembly (20) comprises a body (22) including a pistol grip (24) and a pair of buttons (26). Handle assembly (20) also includes a trigger (28) that is pivotable toward and away from pistol grip (24). It should be understood, however, that various other suitable configurations may be used, including but not limited to a scissor grip configuration. End effector (40) includes an ultrasonic blade (100) and a pivoting clamp arm (44). Clamp arm (44) is coupled with trigger (28) such that clamp arm (44) is pivotable toward ultrasonic blade (100) in response to pivoting of trigger (28) toward pistol grip (24); and such that clamp arm (44) is pivotable away from ultrasonic blade (100) in response to pivoting of trigger (28) away from pistol grip (24). Various suitable ways in which clamp arm (44) may be coupled with trigger (28) will be apparent to those of ordinary skill in the art in view of the teachings herein. In some versions, one or more resilient members are used to bias clamp arm (44) and/or trigger (28) to the open position shown in FIG. 1.

An ultrasonic transducer assembly (12) extends proximally from body (22) of handle assembly (20). Transducer assembly (12) is coupled with a generator (16) via a cable (14). Transducer assembly (12) receives electrical power from generator (16) and converts that power into ultrasonic vibrations through piezoelectric principles. Generator (16) may include a power source and control module that is configured to provide a power profile to transducer assembly (12) that is particularly suited for the generation of ultrasonic vibrations through transducer assembly (12). By way of example only, generator (16) may comprise a GEN 300 sold by Ethicon Endo-Surgery, Inc. of Cincinnati, Ohio. In addition or in the alternative, generator (16) may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on May 24, 2015, the disclosure of which is incorporated by reference herein. It should also be understood that at least some of the functionality of generator (16) may be integrated into handle assembly (20), and that handle assembly (20) may even include a battery or other on-board power source such that cable (14) is omitted. Still other suitable forms that generator (16) may take, as well as various features and operabilities that generator (16) may provide, will be apparent to those of ordinary skill in the art in view of the teachings herein.

Ultrasonic vibrations that are generated by transducer assembly (12) are communicated along an acoustic waveguide (150) (shown in FIGS. 11-12), which extends through shaft assembly (30) to reach ultrasonic blade (100). Blade (100) is thus operable to effectively cut through and seal tissue, particularly when the tissue is being clamped between clamp arm (44) and blade (100). It should be understood that waveguide (150) may be configured to amplify mechanical vibrations transmitted through waveguide (150). Furthermore, waveguide (150) may include features operable to control the gain of the longitudinal vibrations along waveguide (150) and/or features to tune the waveguide (150) to the resonant frequency of the system. Buttons (26) are operable to selectively activate transducer assembly (12), to thereby activate ultrasonic blade (100). In the present example, two buttons (26) are provided—one for activating ultrasonic blade (100) at a low power and another for activating ultrasonic blade (100) at a high power. However, it should be understood that any other suitable number of buttons and/or otherwise selectable power levels may be provided.

In the present example, the distal end of ultrasonic blade (100) is located at a position corresponding to an anti-node associated with resonant ultrasonic vibrations communicated through the waveguide, in order to tune the acoustic assembly to a preferred resonant frequency $f_o$ when the acoustic assembly is not loaded by tissue. When transducer assembly (12) is energized, the distal end of ultrasonic blade (100) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (12) of the present example is activated, these mechanical oscillations are transmitted through the waveguide to reach ultrasonic blade (100), thereby providing oscillation of ultrasonic blade (100) at the resonant ultrasonic frequency. Thus, when tissue is secured between ultrasonic blade (100) and clamp arm (44), the ultrasonic oscillation of ultrasonic blade (100) may simultaneously sever the tissue and denature the proteins in adjacent tissue cells, thereby providing a coagulative effect with relatively little thermal spread. When transducer assembly (12) and ultrasonic blade (100) are not energized, clamp arm (44) may be pivoted relative to ultrasonic blade (100) to grasp and manipulate tissue without cutting or damaging the tissue.

In some versions, an electrical current may also be provided through ultrasonic blade (100) and clamp arm (44) to also cauterize the tissue. While some configurations for an acoustic transmission assembly and transducer assembly (12) have been described, still other suitable configurations for an acoustic transmission assembly and transducer assembly (12) will be apparent to one or ordinary skill in the art in view of the teachings herein. Similarly, other suitable configurations for end effector (40) will be apparent to those of ordinary skill in the art in view of the teachings herein.

In the present example, shaft assembly (30) is configured to selectively couple with transducer assembly (12). To assist in proper coupling, a torque wrench (not shown) may be included about shaft assembly (30). Such a torque wrench may be configured to facilitate gripping of shaft assembly (30) as shaft assembly (30) is rotated relative to transducer assembly (12) during coupling. In addition, such a torque wrench may be configured to provide audible and/or tactile feedback once the appropriate amount of torque as been achieved to provide a coupling of transducer assembly (12) and shaft assembly (30) at the appropriate tightness. For instance, a torque wrench may provide a pair of audible and tactile clicks once the appropriate level of torque/tightness has been achieved. Other variations of a torque wrench will be apparent to those of ordinary skill in the art in view of the teachings herein. Furthermore, it should be understood that a torque wrench may simply be omitted, if desired.

In some versions, shaft assembly (30) includes an articulation section enabling end effector (40) to be angularly deflected laterally away from the longitudinal axis defined by shaft assembly (30). By way of example only, such an articulation section may be configured in accordance with one or more teachings of U.S. Pub. No. 2012/0078247, issued as U.S. Pat. No. 9,402,682 on Aug. 2, 2016, the disclosure of which is incorporated by reference herein. As another merely illustrative example, such an articulation section may be configured in accordance with one or more teachings of U.S. patent application Ser. No. 13/538,588, issued as U.S. Pat. No. 9,393,037 on Jun. 19, 2016 and/or U.S. patent application Ser. No. 13/657,553, issued as U.S. Pat. No. 9,095,367 on Aug. 4, 2015, the disclosures of which are incorporated by reference herein. Of course, some versions of shaft assembly (30) may simply lack articulation altogether. Shaft assembly (30) of the present example comprises a knob (32) that is operable to rotate shaft assembly (30) and end effector (40) relative to handle assembly (20), about the longitudinal axis of shaft assembly (30). However, it should be understood that knob (32) and rotatability of shaft assembly (30) are merely optional.

The foregoing components and operabilities of instrument (10) are merely illustrative. Instrument (10) may be configured in numerous other ways as will be apparent to those of ordinary skill in the art in view of the teachings herein. By way of example only, at least part of instrument (10) may be constructed and/or operable in accordance with at least some of the teachings of any of the following, the disclosures of which are all incorporated by reference herein: U.S. Pat. Nos. 5,322,055; 5,873,873; 5,980,510; 6,325,811; 6,773,444; 6,783,524; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940, now abandoned; U.S. Pub. No. 2009/0105750, issued as U.S. Pat. No. 8,623,027 on Jan. 7, 2014; U.S. Pub. No. 2010/0069940, issued as U.S. Pat. No. 9,023,071 on May 5, 2015; U.S. Pub. No. 2011/0015660, issued as U.S. Pat. No. 8,461,744 on Jun. 11, 2013; U.S. Pub. No. 2012/0112687, issued as U.S. Pat. No. 9,381,058 on Jun. 5, 2016; U.S. Pub. No. 2012/0116265, now abandoned; U.S. patent application Ser. No. 13/538,588, issued as U.S. Pat. No. 9,393,037 on Jun. 19, 2016; U.S. patent application Ser. No. 13/657,553, issued as U.S. Pat. No. 9,095,367 on Aug. 4, 2015; and/or U.S. Pat. App. No. 61/410,603. Additional variations for instrument (10) will be described in greater detail below. It should be understood that the below described variations may be readily applied to any of the instruments referred to in any of the references that are cited herein, among others.

II. Exemplary Ultrasonic Blade Configuration

FIGS. 2-9 show ultrasonic blade (100) of instrument (10) in greater detail. Ultrasonic blade (100) of the present example is in the form of a tapered multi-functional curved blade with functional asymmetries and minimized undesirable motion. It should be understood that providing a curved version of ultrasonic blade (100) introduces a set of engineering considerations that may need to be addressed. For instance, a curved ultrasonic blade (100) may need to be properly balanced, including careful positioning of the mass along end effector (40). Another aspect of proper balancing may include a desire to separately balance orthogonal displacements encountered by an activated ultrasonic blade (100), which may be particularly challenging when blade (100) is curved. In addition, a curved ultrasonic blade (100) may be prone to fracture due to high stresses in the curved region of blade (100), particularly if blade (100) comes into contact with metal when blade (100) is in an activated state. Furthermore, a curved ultrasonic blade (100) may provide a relatively shorter active length, which may in turn limit the size of the vessel (or other tissue structure) that may be operated on by blade (100). ("Active length" may be defined as the as the length from the distal end (102) of blade (100) to where the displacement is one half of the displacement at its distal end (102).) Blade (100) of the present example accounts for the foregoing considerations.

With the above-noted engineering considerations addressed, it should also be understood that the curved and tapered configuration of blade (100) may provide surgical benefits such as improved surgeon visibility. In addition, the curve and taper may together provide a longer active length through increased speed of sound and progressive reduction in mass. Also, the taper may results in a smaller surface at distal end (102), which may improve piercing/dissection capability by increasing local pressure imparted on tissue. Robust performance may be improved by controlling the ratio of acoustic stress to bending stress in the exposed portion of blade (100). Blade (100) may thus be less sensitive to damage from inadvertent contact with other metallic material for improved life.

Blade (100) of the present example is positioned at the distal end of waveguide (150). The proximal end of waveguide (150) is coupled with transducer assembly (12). Thus, blade (100) and waveguide (150) together define an acoustic transmission assembly that is acoustically coupled with transducer assembly (12). By way of example only, this acoustic transmission assembly may be approximately 36 cm in length, approximately 23 cm in length, or any other suitable length. In the present example, distal end (102) of ultrasonic blade (42) is located at a position corresponding to an anti-node associated with resonant ultrasonic vibrations communicated through waveguide (150), in order to tune the acoustic transmission assembly to a preferred resonant frequency $f_o$ when the acoustic transmission assembly is not loaded by tissue. Blade (100) and waveguide (150) are integrally formed in this example, though blade (100) and waveguide (150) may alternatively be formed as separate pieces that are joined together (e.g., through a threaded coupling, interference fit, welded joint, etc.). Blade (100) may be understood to effectively terminate proximally at the distal-most node associated with resonant ultrasonic vibrations communicated through waveguide (150). In other words, blade (100) extends from the distal-most node to the distal-most anti-node.

When transducer assembly (12) is energized, distal end (102) of ultrasonic blade (100) is configured to move longitudinally (along the x-axis) in the range of, for example, approximately 10 to 500 microns peak-to-peak, and in some instances in the range of about 20 to about 200 microns, at a predetermined vibratory frequency $f_o$ of, for example, 55.5 kHz. When transducer assembly (12) of the present example is activated, these mechanical oscillations are transmitted through waveguide (150) to reach ultrasonic blade (100), thereby providing oscillation of ultrasonic blade (100) at the resonant ultrasonic frequency. Thus, when tissue is secured between ultrasonic blade (100) and clamp arm (44), the ultrasonic oscillation of ultrasonic blade (100) may simultaneously sever the tissue and denature the proteins in adjacent tissue cells, thereby providing a coagulative effect with relatively little thermal spread.

Blade (100) of the present example is tapered from its proximal end toward distal end (102). Blade (100) is also curved such that the center of distal end (102) is positioned lateral to the longitudinal axis defined by waveguide (150). It should be understood that certain balance features may be required to maintain longitudinal motion substantially along the x-axis and within the x-y plane and also to separate transverse mode ranges of vibration away from the desired longitudinal mode of vibration at a resonant frequency of 55.5 kHz. As will be described in greater detail below, waveguide (150) includes a series of gain steps that are configured to provide a gain of approximately 3.5, such that distal end (102) of blade (100) will vibrate along the x-axis at a maximum excursion of approximately 73.5 microns at maximum power generation (e.g., such that the excursion of transducer (150) is approximately 21.5 microns).

Figure 7:
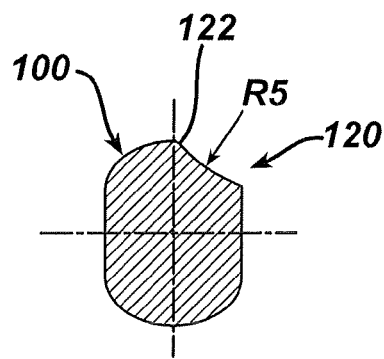
FIG. 7 depicts a cross-sectional view of the ultrasonic blade of FIG. 2, taken along line 7-7 of FIG. 6.
Figure 8:
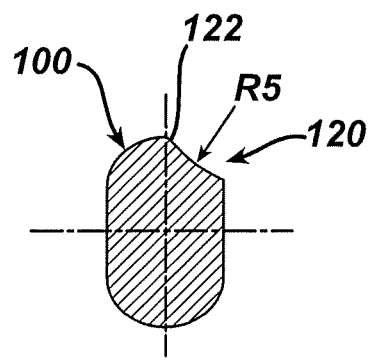
FIG. 8 depicts a cross-sectional view of the ultrasonic blade of FIG. 2, taken along line 8-8 of FIG. 6.
Figure 9:
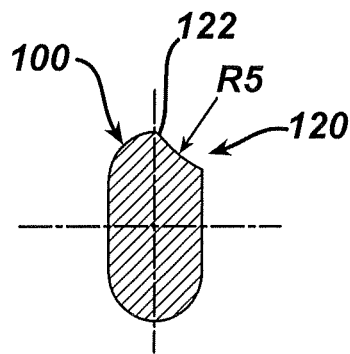
FIG. 9 depicts a cross-sectional view of the ultrasonic blade of FIG. 2, taken along line 9-9 of FIG. 6.

The taper of blade (100) is best seen in FIGS. 7-9, which shows a set of cross-sections at various locations along the length of blade (100). In particular, FIG. 7 shows a proximal cross-section of blade (100) along a plane that runs along an axis (PA) that is perpendicular to the longitudinal axis of waveguide (150). FIG. 8 shows an intermediate cross-section of blade (100) along a first plane that is obliquely oriented relative to the axis (PA). FIG. 9 shows a distal cross-section of blade (100) along a second plane that is obliquely oriented relative to the axis (PA). In the present example, the width of blade (100) in the cross-section shown in FIG. 7 is between about 0.055 inches and about 0.070 inches, and more particularly between about 0.060 inches and about 0.065 inches. The width of blade (100) in the cross-section shown in FIG. 8 is between about 0.045 inches and about 0.060 inches, and more particularly between about 0.050 inches and about 0.055 inches. The width of blade (100) in the cross-section shown in FIG. 9 is between about 0.035 and 0.050 inches, and more particularly between about 0.040 inches and about 0.045 inches. Of course, any other suitable dimensions may be used.

Figure 4:
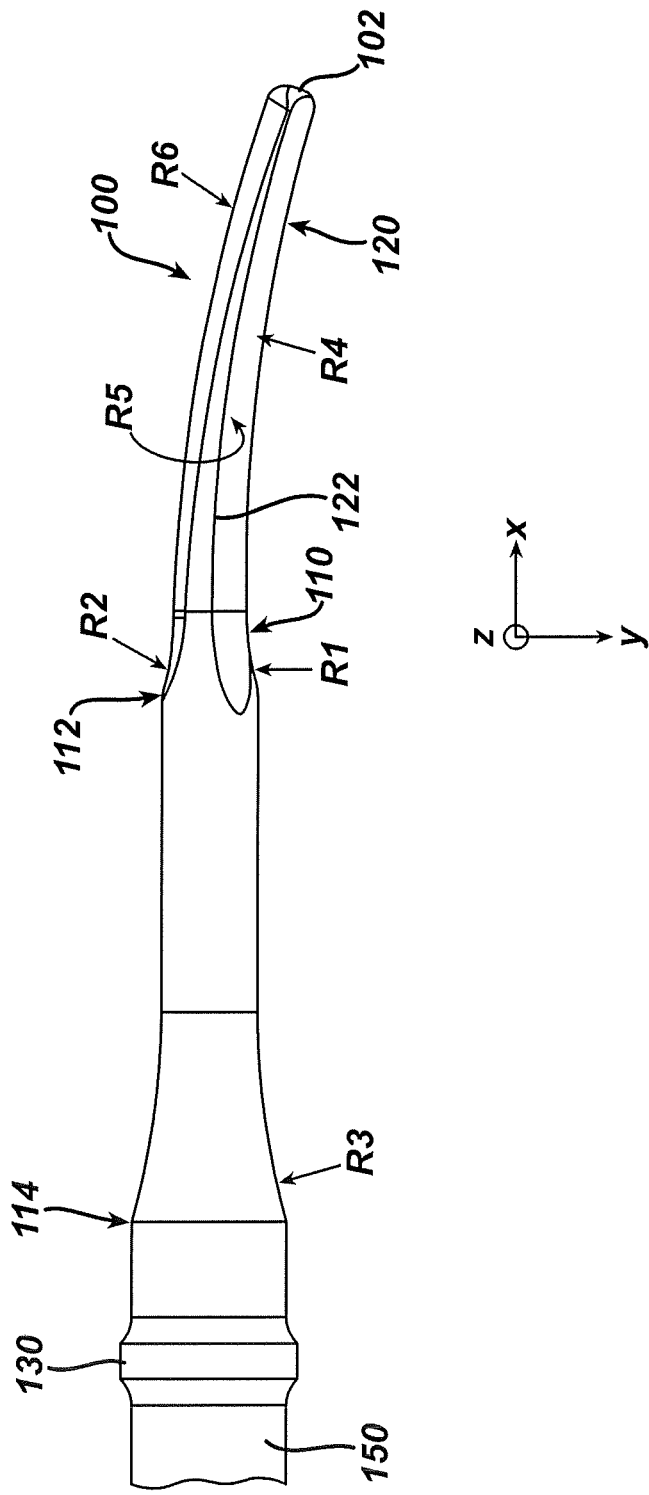
FIG. 4 depicts a top plan view of the ultrasonic blade of FIG. 2.
Figure 5:
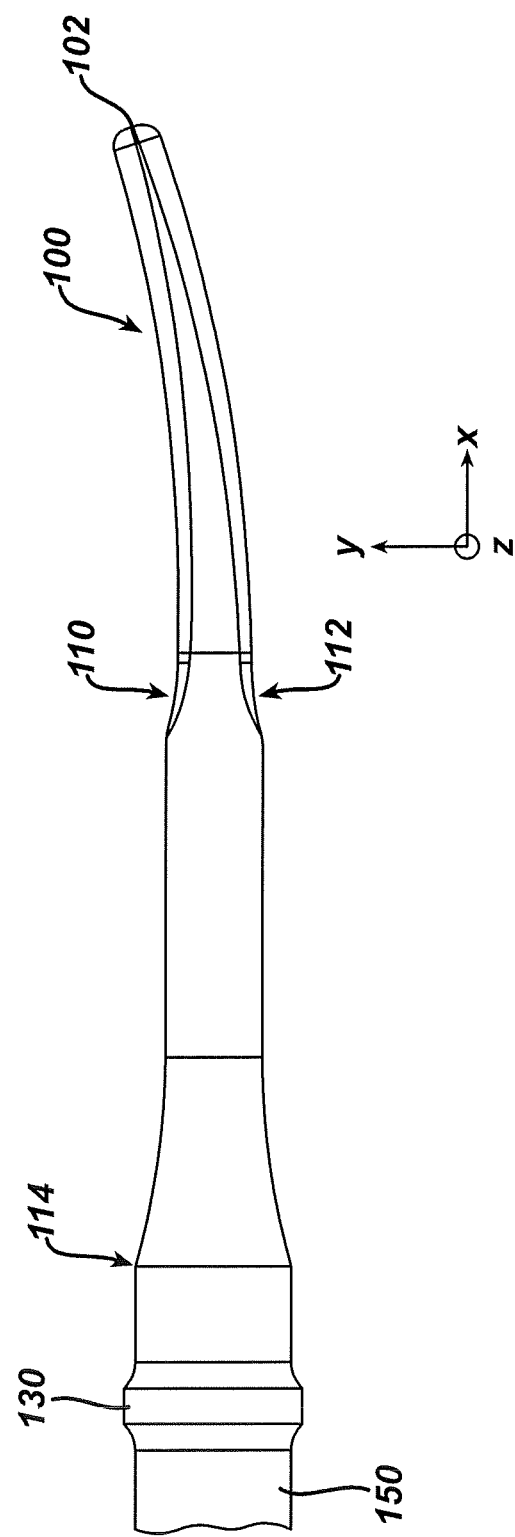
FIG. 5 depicts a bottom plan view of the ultrasonic blade of FIG. 2.
Figure 6:
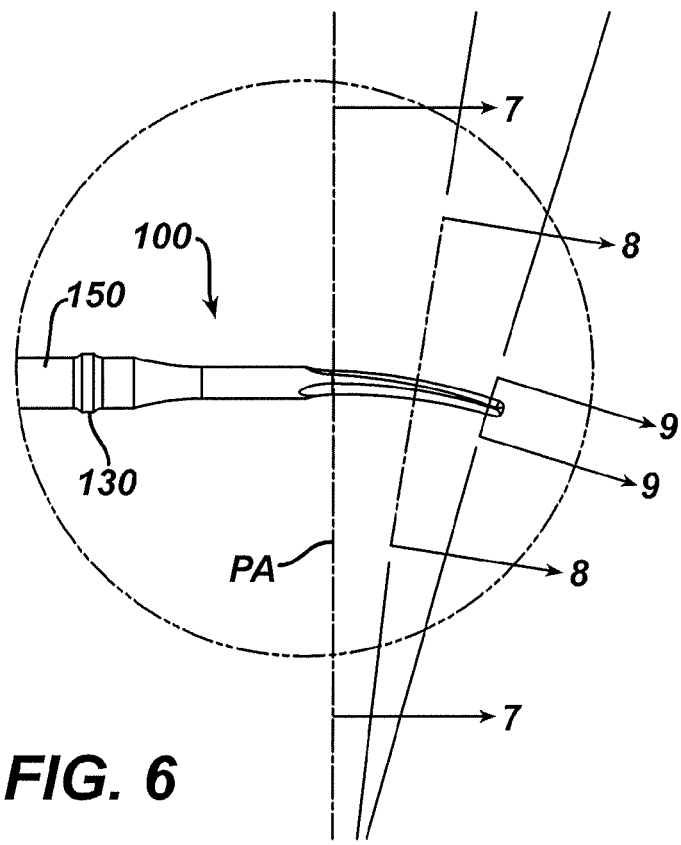
FIG. 6 depicts a top plan view of the ultrasonic blade of FIG. 2, with several cross-sectional planes indicated.

The curves and taper blade (100) are defined by simple radial cuts, as well as more complex compound radii cuts, which are made in a base curved cylinder. These cuts define a plurality of balance features (110, 112, 114, 120). In particular, and as best seen in FIG. 4, a first balance feature (110) is formed by a lateral concave cut having a first radius of curvature (R1). By way of example only, the first radius of curvature (R1) may be between about 0.200 inches and about 0.250 inches, and more particularly about 0.225 inches. Of course, any other suitable value may be used for the first radius of curvature (R1). In the present example, first balance feature (110) is defined by the first radius of curvature (R1) swept along an orthogonal x-y plane that passes through the longitudinal axis of shaft assembly (30). A second balance feature (112) is formed by a lateral concave cut having a second radius of curvature (R2) swept along an orthogonal x-y plane that passes through the longitudinal axis of shaft assembly (30). By way of example only, the second radius of curvature (R2) may be between about 0.250 inches and about 0.275 inches, and more particularly about 0.268 inches. Of course, any other suitable value may be used for the second radius of curvature (R2). In the present example, second balance feature (112) is offset from first balance feature (110) along the length of blade (100). In particular, second balance feature (112) is located further distal than first balance feature (110) by between about 0.002 inches and about 0.010 inches, and more particularly about 0.005 inches. Alternatively, any other suitable offset (or no offset at all) may be used. In the present example, second balance feature (112) is defined by the second radius of curvature (R2) swept along the same orthogonal x-y plane that passes through the longitudinal axis of shaft assembly (30) as the orthogonal x-y plane associated with first balance feature (110) and first radius of curvature (R1).

A third balance feature (114) extends circumferentially about blade (100) and is formed by a concave cut having a third radius of curvature (R3). By way of example only, the third radius of curvature (R3) may be between about 0.600 inches and about 0.700 inches, and more particularly about 0.650 inches. Of course, any other suitable value may be used for the third radius of curvature (R3).

A fourth balance feature (120) is best seen in FIGS. 4 and 7-8. Fourth balance feature (120) is formed as a longitudinally extending convex recess in one corner of blade (100). The recess of balance feature (120) is defined by a fourth radius of curvature (R4) that is swept along the x-y plane and a fifth radius of curvature (R5) that is swept along the y-z plane. By way of example only, the fourth radius of curvature (R4) may be between approximately 1.350 inches and approximately 1.425 inches, and more particularly about 1.395 inches. Alternatively, any other suitable value may be used for the fourth radius of curvature (R4). In the present example, the x-y plane along which the fourth radius of curvature (R4) is swept is parallel to yet spaced apart from the x-y plane along which the first and second radii of curvature (R1, R2) are swept. Also by way of example only, the fifth radius of curvature (R5) may be between approximately 0.060 inches and approximately 0.065 inches, and more particularly about 0.062 inches. Alternatively, any other suitable value may be used for the fifth radius of curvature (R5). Fourth balance feature (120) may be configured to balance motion of blade (100) as described in U.S. Pat. No. 6,773,444, the disclosure of which is incorporated by reference herein. In addition, fourth balance feature (120) presents an edge (122) that may be used to back-cut tissue and/or for other purposes. In some versions of instrument (10) that have clamp arm (44), ultrasonic blade (100) is oriented such that edge (122) faces toward clamp arm (44). In some other versions of instrument (10) that have clamp arm (44), ultrasonic blade (100) is oriented such that edge (122) faces away from clamp arm (44).

As can be seen in FIG. 4, the lateral concave cut of second balance feature (112) transitions into a convex curve extending to distal end (102). This convex curve is defined by a sixth radius of curvature (R6) swept along an orthogonal x-y plane that passes through the longitudinal axis of shaft assembly (30). By way of example only, the sixth radius of curvature (R6) may be approximately 1.446 inches. Of course, any other suitable value may be used for the sixth radius of curvature (R6).

Figure 10:
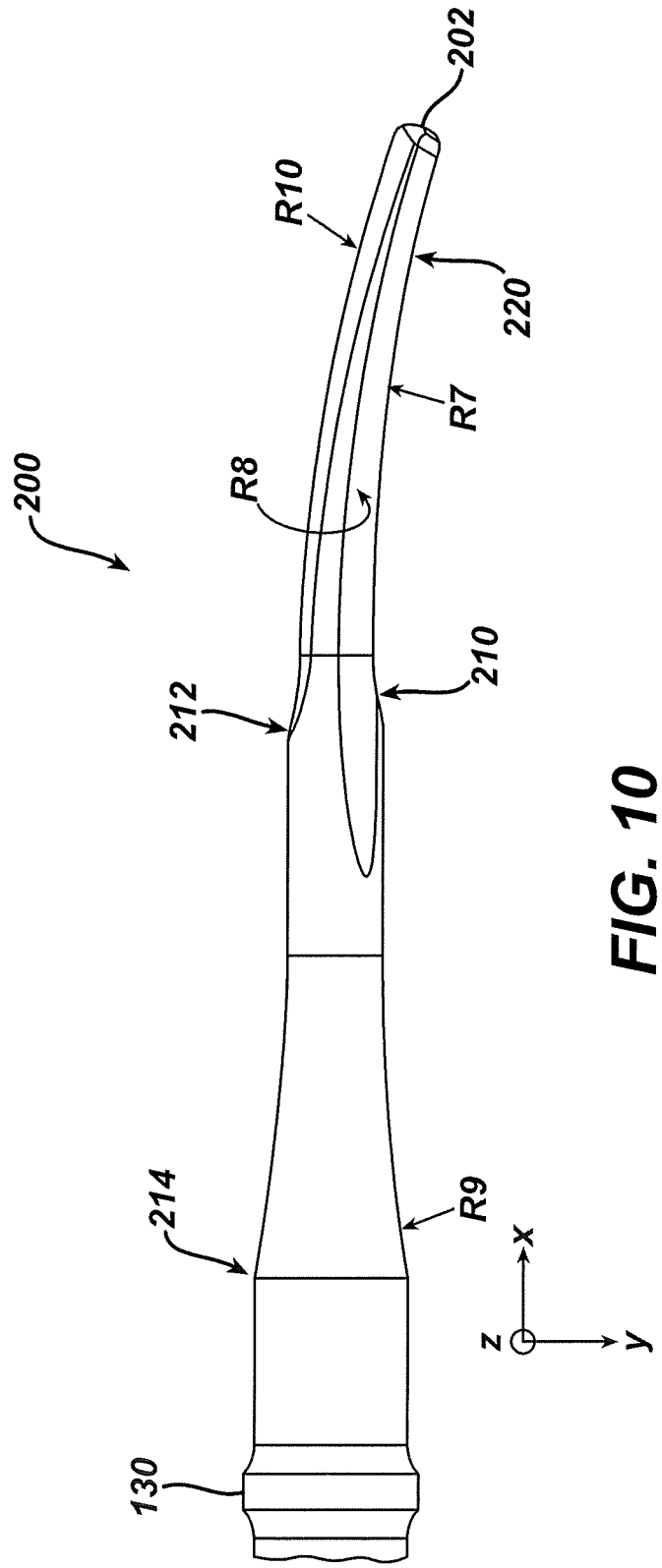
FIG. 10 depicts a top plan view of an exemplary alternative ultrasonic blade suited for incorporation in the instrument of FIG. 1.

FIG. 10 shows an exemplary alternative ultrasonic blade (200) that may be located at the distal end of waveguide (150). Blade (200) of this example is substantially similar to blade (100) described above and includes a distal end (202) and a plurality of balance features (210, 212, 214, 220). In some versions, blade (100) is approximately 36 centimeters in length while blade (200) is approximately 23 centimeters in length. Of course, any other suitable dimensions may be used. The differences in the radii of curvature associated with blade (200) may be selected to account for blade (200) having a shorter length than blade (100).

In the example shown in FIG. 10, balance features (210, 212) of blade (200) are substantially identical to respective balance features (110, 112) of blade (100), including having the same radii of curvature as balance features (110, 112). While balance feature (220) of blade (200) is also similar to balance feature (120) of blade (100), balance feature (220) is defined by radii of curvature (R7, R8) that differ from the respective radii of curvature (R4, R5) that define balance feature (120). In particular, the recess of balance feature (220) is defined by a seventh radius of curvature (R7) that is swept along the x-y plane and an eighth radius of curvature (R8) that is swept along the y-z plane. By way of example only, the seventh radius of curvature (R7) may be between approximately 1.390 inches and approximately 1.500 inches, and more particularly about 1.420 inches. In some other versions, the seventh radius of curvature (R7) is approximately 1.395 inches. Alternatively, any other suitable value may be used for the seventh radius of curvature (R7). Also by way of example only, the eighth radius of curvature (R8) may be between approximately 1.000 inches and approximately 1.200 inches, and more particularly about 1.100 inches. In some other versions, the eighth radius of curvature (R8) is approximately 1.395 inches. Alternatively, any other suitable value may be used for the eighth radius of curvature (R8).

Blade (200) of FIG. 10 also has a circumferentially extending balance feature (214) defined by a ninth radius of curvature (R9) that is approximately 1.500 inches. Alternatively, any other suitable value may be used for the ninth radius of curvature (R9). The lateral concave cut of balance feature (212) transitions into a convex curve extending to distal end (202). This convex curve is defined by a tenth radius of curvature (R10) swept along an orthogonal x-y plane that passes through the longitudinal axis of shaft assembly (30). By way of example only, the tenth radius of curvature (R10) may be approximately 1.395 inches. Of course, any other suitable value may be used for the tenth radius of curvature (R10). As noted above, in some instances an ultrasonic blade having a length of approximately 36 cm is configured in accordance with blade (100); while an ultrasonic blade having a length of approximately 23 cm is configured in accordance with blade (200). Alternatively, the configuration of either blade (100, 200) may be combined with any other suitable ultrasonic blade length.

Figure 11:
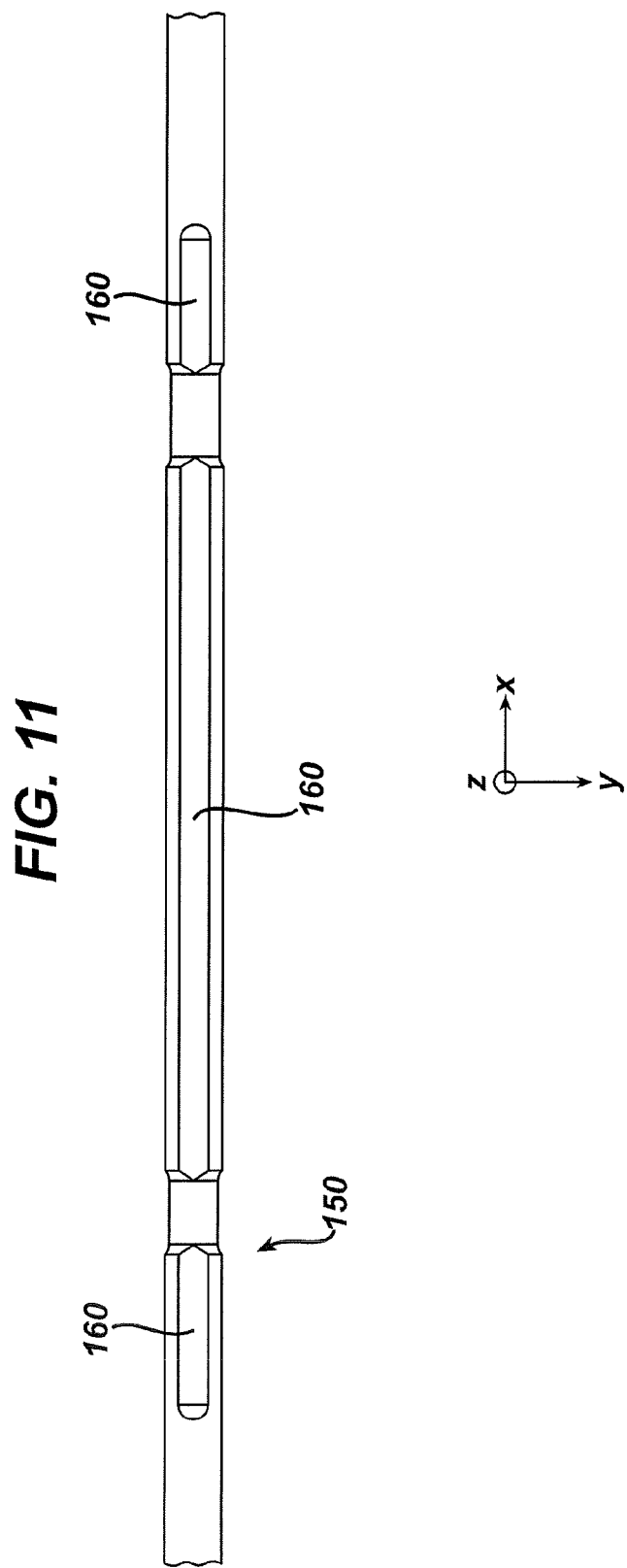
FIG. 11 depicts a side elevational view of a portion of an acoustic waveguide of the surgical instrument of FIG. 1.
Figure 12:
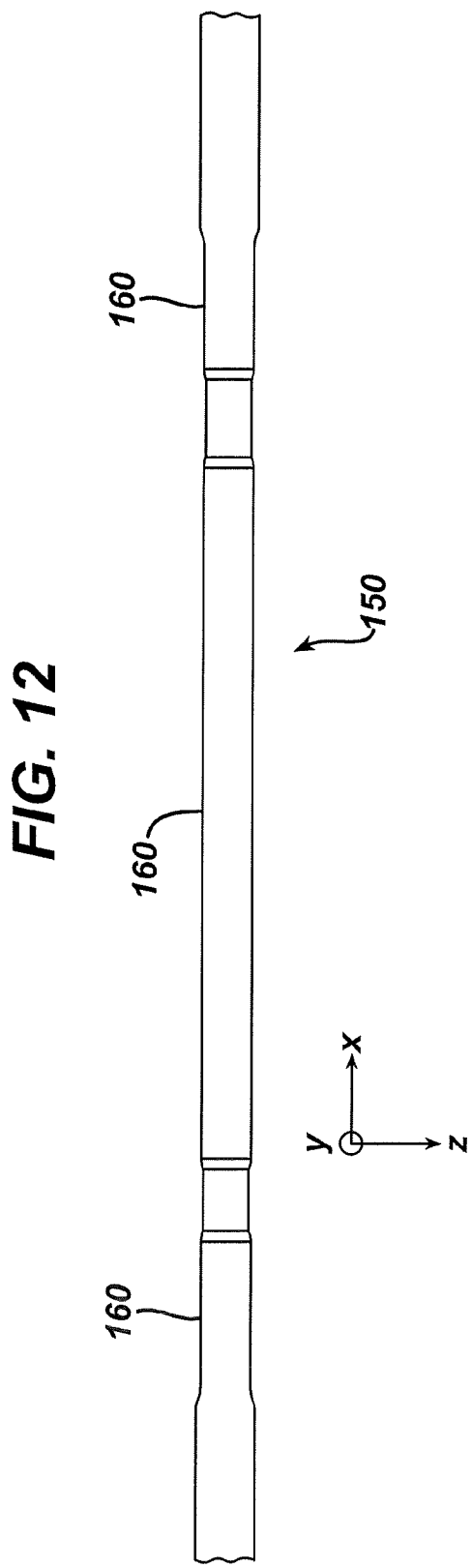
FIG. 12 depicts a top plan view of the portion of the acoustic waveguide of FIG. 11.

FIGS. 11-12 show waveguide (150) of the present example in greater detail. Waveguide (150) may be flexible, semi-flexible or rigid. Waveguide (150) may also be configured to amplify the mechanical vibrations transmitted through waveguide (150) to blade (100) as is well known in the art. Waveguide (150) may further have features to control the gain of the longitudinal vibration along waveguide (150) and features to tune waveguide (150) to the resonant frequency of the system. In particular, waveguide (150) may have any suitable cross-sectional dimension. For example, waveguide (150) may be tapered at various sections to control the gain of the longitudinal vibration. Waveguide (150) may, for example, have a length substantially equal to an integral number of one-half system wavelengths (nλ/2). The waveguide (150) and blade (100) may be preferably fabricated from a solid core shaft constructed out of material, which propagates ultrasonic energy efficiently, such as titanium alloy (e.g., Ti-6Al-4V), aluminum alloys, sapphire, stainless steel or any other acoustically compatible material. Waveguide (150) may further include at least one radial hole or aperture (not shown) extending therethrough, substantially perpendicular to the longitudinal axis of waveguide (150). Such an aperture may be positioned at a node. A proximal o-ring (not shown) and distal o-ring (130) (see FIGS. 2-6) are assembled onto the acoustic transmission assembly near the ultrasonic nodes of waveguide (150), as is known in the art.

As further shown in FIGS. 11-12, waveguide (150) further includes balance features (160). Balance features (160) are formed as laterally presented flat surfaces on waveguide (150), which is otherwise cylindraceous. Balance features (160) serve to widen the transverse mode ranges away from the preferred longitudinal modes in both directions from the resonant frequency (e.g., 55.5 kHz). In some versions, balance features (160) are spaced 180° apart on waveguide (150) and extend for a length from about 2.600 inches to about 2.800 inches, and more particularly about 2.700 inches. The centerline of balance features (160) is from about 7.000 to about 7.200 inches, and more particularly about 7.148 inches. Alternatively, any other suitable dimensions may be used.

III. Exemplary Control Circuits

In some instances, instrument (10) may include a foot pedal (not used) that provides a switch for selectively energizing transducer (12) and ultrasonic blade (100). Alternatively, the operator may use buttons (26) as switches to selectively energize transducer (12) and ultrasonic blade (100). In some such instances, however, there may be significant variability in the resistance of cable (14) and/or in the resistance of contacts in circuitry between generator (16) and buttons (26). Such variable resistance may make it difficult for generator (16) to detect switch closure states (e.g., when buttons (26) are depressed). Variability in resistance may be due to residue left on contacts of handle assembly (20) by a cleaning process; and/or due to other factors. Some versions of the circuitry may be significantly less susceptible to such risks. For instance, some versions of circuitry may effectively null out the effects of variable resistance in real time. Various examples of such circuitry are described in greater detail below; while still other examples will be apparent to those of ordinary skill in the art in view of the teachings herein.

In some versions, generator (16) comprises a GEN11 generator, manufactured and sold by Ethicon Endo-Surgery, Inc. Generator (16) may act as a constant-current source (e.g., at approximately +/−16 mA, alternating at a low frequency, such as about 500 Hz) and determine the state of the switches (open/closed) in handle assembly (20) by measuring the voltage drop across the handswitch lines, at the face of generator (16). This voltage drop may include an unknown voltage drop caused by the resistance in cable (14) and/or resistance at contacts in handle assembly (20), which may change over time due to factors such as instrument rotation and changes in contact force during instrument usage, etc. The examples described below enable generator (16) to determine and subtract out this unknown voltage drop by measuring a known reference component in handle assembly (20) that produces a known voltage drop, in close time proximity to measuring the switch states.

Figure 13:
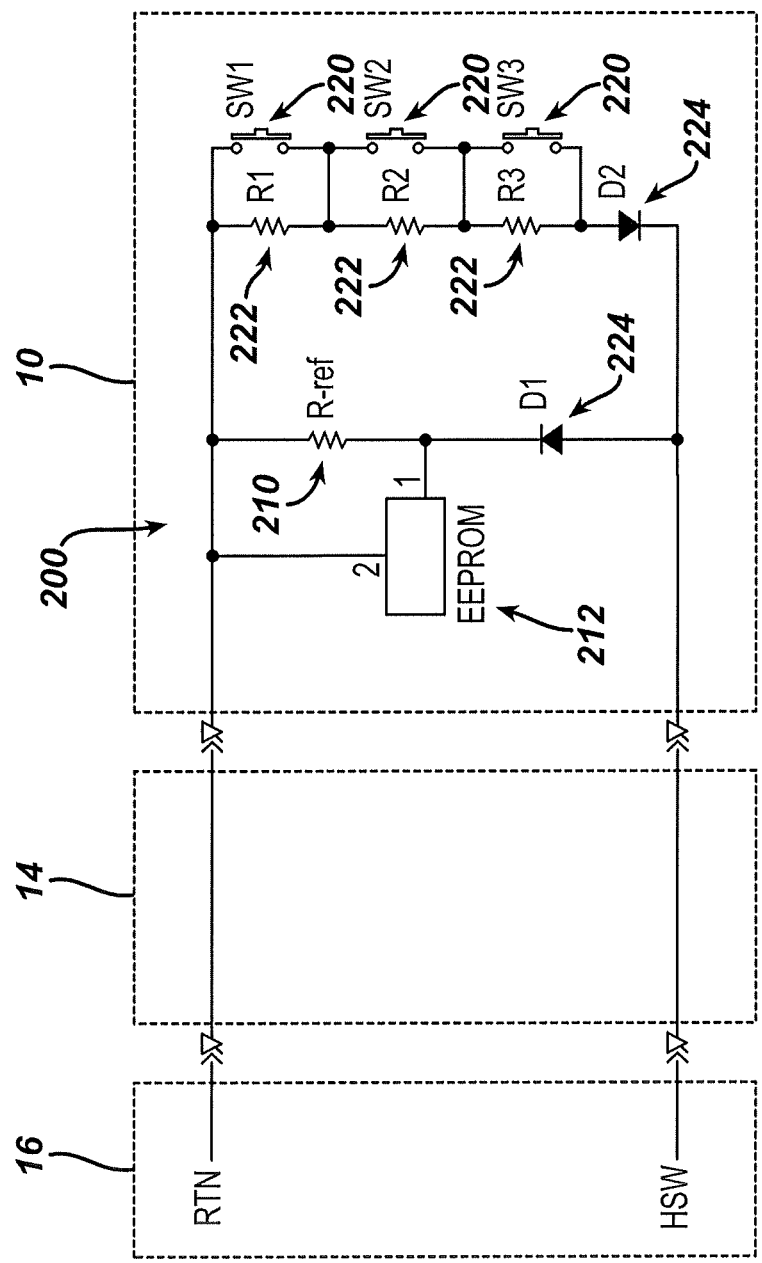
FIG. 13 depicts a schematic view of an exemplary circuit suited for incorporation in the instrument of FIG. 1.

FIG. 13 shows one merely exemplary circuit (200) that may be incorporated into instrument (10) to account for variations in resistance as described above. Circuit (200) includes a reference resistor (210) and an EEPROM (212) that together provide a reference feature placed on the positive leg of circuit (200). This reference feature formed by reference resistor (210) and EEPROM (212) may be read on the positive half-cycle of an interrogation signal from generator (16). It should be understood that EEPROM (212) draws such low current that EEPROM (212) will not appreciably affect the voltage drop produced by reference resistor (210). Circuit (200) also includes a set of switches (220), respective resistors (222), and a pair of diodes (224). Switches (220) are actuated by buttons (26), trigger (28), and/or other movable features in handle assembly (20). Switches (220), resistors (222), and diodes (224) are placed on the negative leg of circuit (200). Switches (220), resistors (222), and diodes (224) are thus read on the negative half-cycle of an interrogation signal from generator (16). Generator (16) is operable to determine and subtract out a voltage drop from switches (220), resistors (222), and diodes (224) based on a known voltage drop from reference resistor (210), in close time proximity to measuring the states of switches (220).

Figure 14:
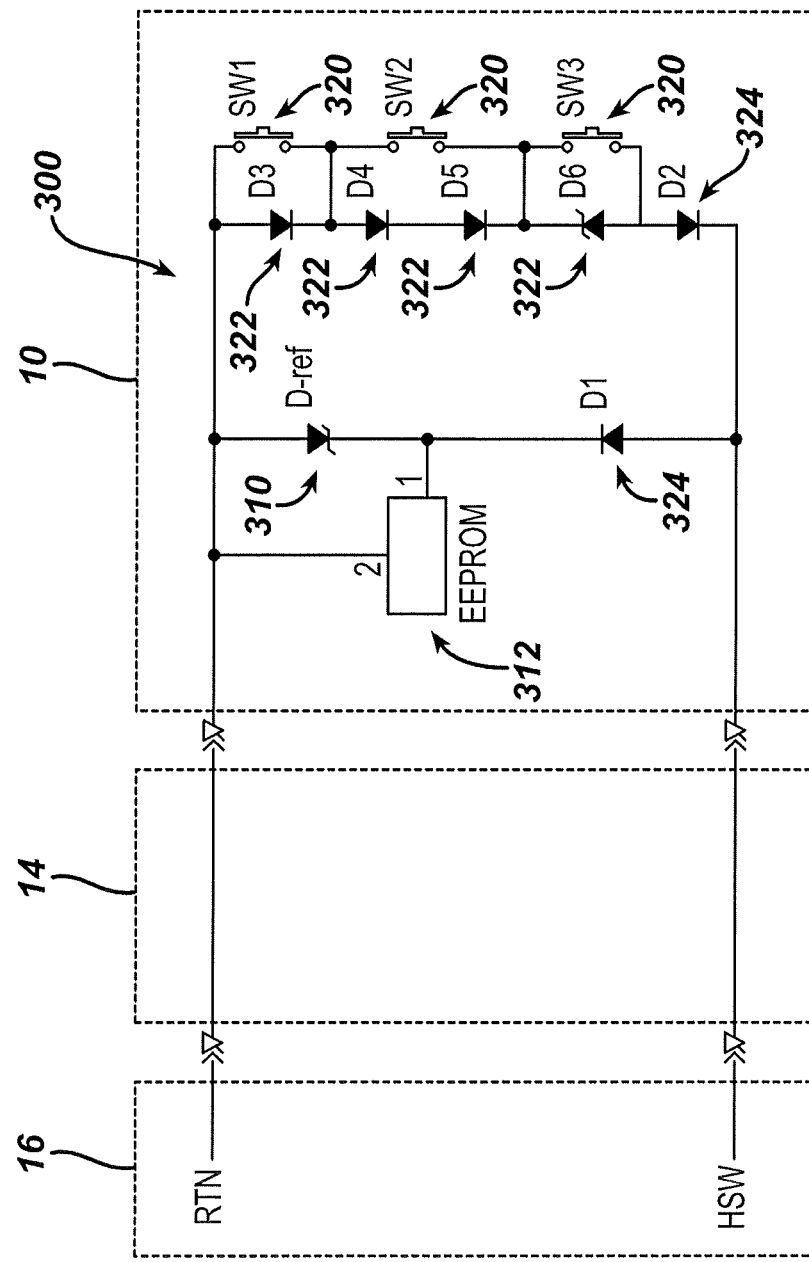
FIG. 14 depicts a schematic view of another exemplary circuit suited for incorporation in the instrument of FIG. 1.

FIG. 14 shows another merely exemplary circuit (300) that may be incorporated into instrument (10) to account for variations in resistance as described above. Circuit (300) includes a reference zener diode (310) and an EEPROM (312) that together provide a reference feature placed on the positive leg of circuit (300). This reference feature formed by reference zener diode (310) and EEPROM (312) may be read on the positive half-cycle of an interrogation signal from generator (16). It should be understood that EEPROM (312) draws such low current that EEPROM (312) will not appreciably affect the voltage drop produced by zener diode (310). Circuit (300) also includes a set of switches (320), respective diodes (322), and an additional pair of diodes (324). Switches (320) are actuated by buttons (26), trigger (28), and/or other movable features in handle assembly (20). Switches (320) and diodes (322, 324) are placed on the negative leg of circuit (300). Switches (320) and diodes (322, 324) are thus read on the negative half-cycle of an interrogation signal from generator (16). Generator (16) is operable to determine and subtract out a voltage drop from switches (320) and diodes (322, 324) based on a known voltage drop from reference zener diode (310), in close time proximity to measuring the states of switches (320).

Figure 15:
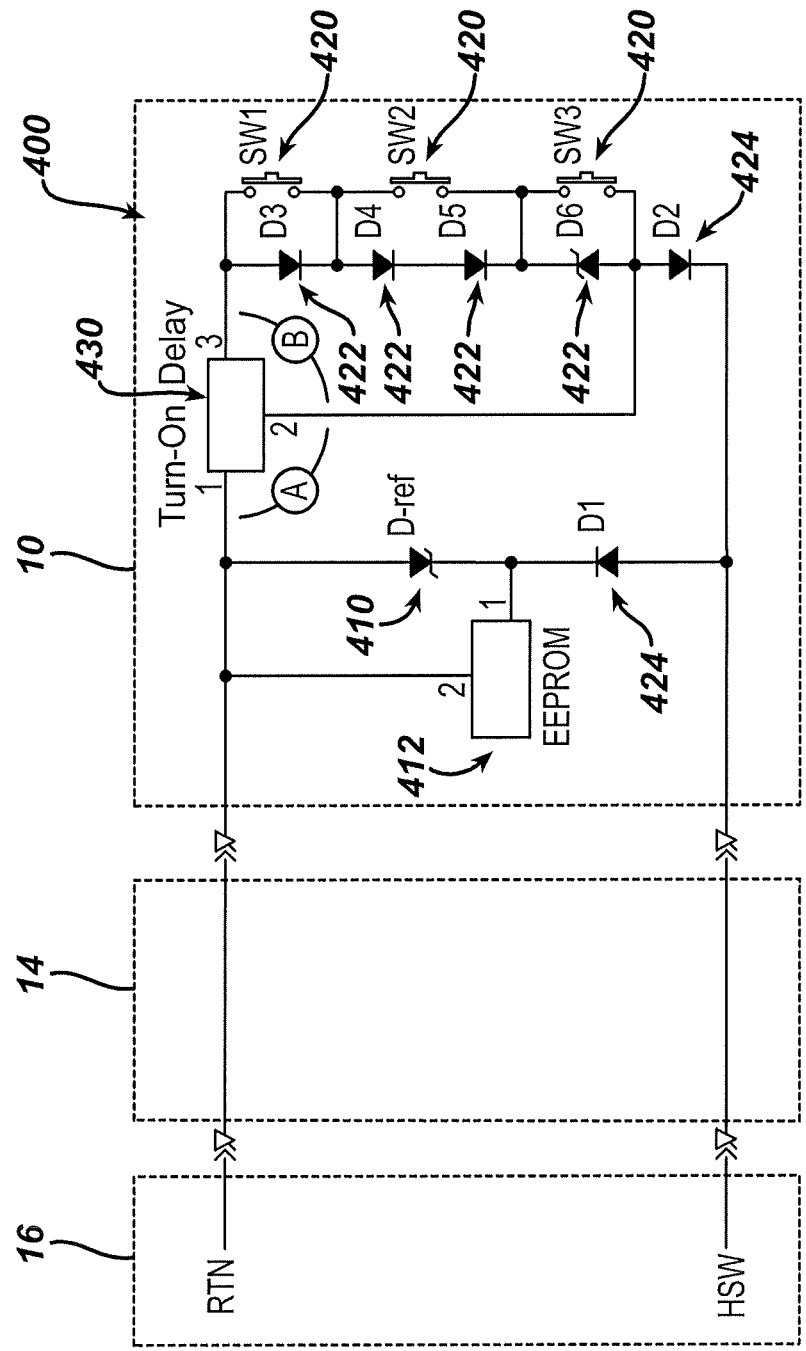
FIG. 15 depicts a schematic view of another exemplary circuit suited for incorporation in the instrument of FIG. 1.

FIG. 15 shows another merely exemplary circuit (400) that may be incorporated into instrument (10) to account for variations in resistance as described above. Circuit (400) is substantially similar to circuit (300) described above, in that circuit (400) includes a reference zener diode (410), an EEPROM (412), switches (420), and diodes (422, 424) that are all arranged in a manner similar to the arrangement of zener diode (310), EEPROM (312), switches (320), and diodes (322, 324) of circuit (300). Unlike circuit (300), circuit (400) of this example further includes a turn-on delay circuit (430). Turn-on delay circuit (430) is set to approximately ¼ of the interrogation signal cycle-time of generator (16), so that generator (16) sees only the reference feature (i.e., zener diode (410) and EEPROM (412)) during the first half of the negative half-cycle; and then sees switches (420), and diodes (422, 424) in parallel with the reference feature during the second half of the negative half-cycle. In some versions, turn-on delay circuit (430) may include a Maxim MAX6895 sequencer driving a Philips PMV65XP p-channel FET. Other suitable configurations for turn-on-delay circuit (430) will be apparent to those of ordinary skill in the art in view of the teachings herein.

Figure 16:
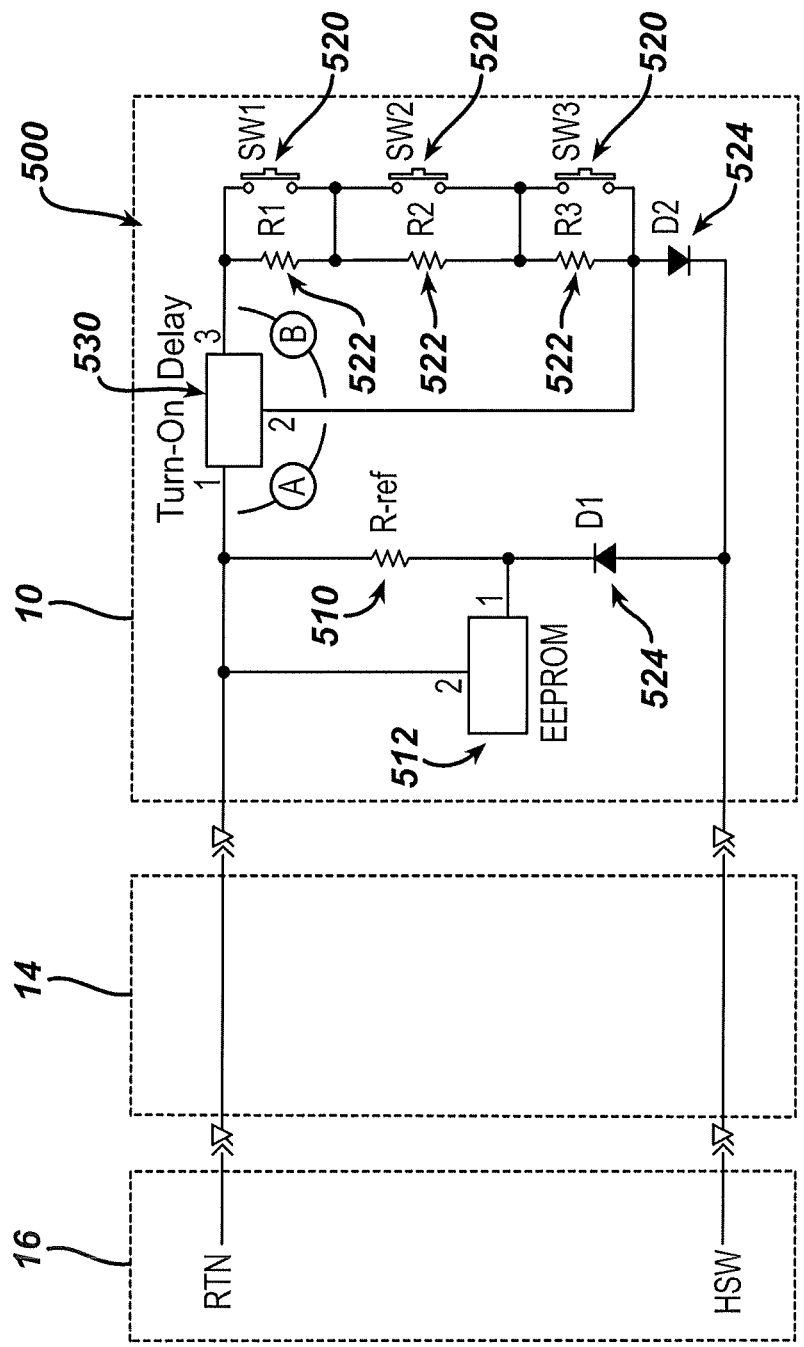
FIG. 16 depicts a schematic view of another exemplary circuit suited for incorporation in the instrument of FIG. 1.

FIG. 16 shows another merely exemplary circuit (500) that may be incorporated into instrument (10) to account for variations in resistance as described above. Circuit (500) is substantially similar to circuit (200) described above, in that circuit (200) includes a reference resistor (510), an EEPROM (512), switches (520), resistors (522), and diodes (524) that are all arranged in a manner similar to the arrangement of reference resistor (210), an EEPROM (212), switches (220), resistors (222), and diodes (224) of circuit (200). Unlike circuit (200), circuit (500) of this example further includes a turn-on delay circuit (530). Turn-on delay circuit (530) is set to approximately ¼ of the interrogation signal cycle-time of generator (16), so that generator (16) sees only the reference feature (i.e., reference resistor (510) and EEPROM (512)) during the first half of the negative half-cycle; and then sees switches (520), resistors (522), and diodes (524) in parallel with the reference feature during the second half of the negative half-cycle. In some versions, turn-on delay circuit (530) may include a Maxim MAX6895 sequencer driving a Philips PMV65XP p-channel FET. Other suitable configurations for turn-on-delay circuit (530) will be apparent to those of ordinary skill in the art in view of the teachings herein.

Figure 17:
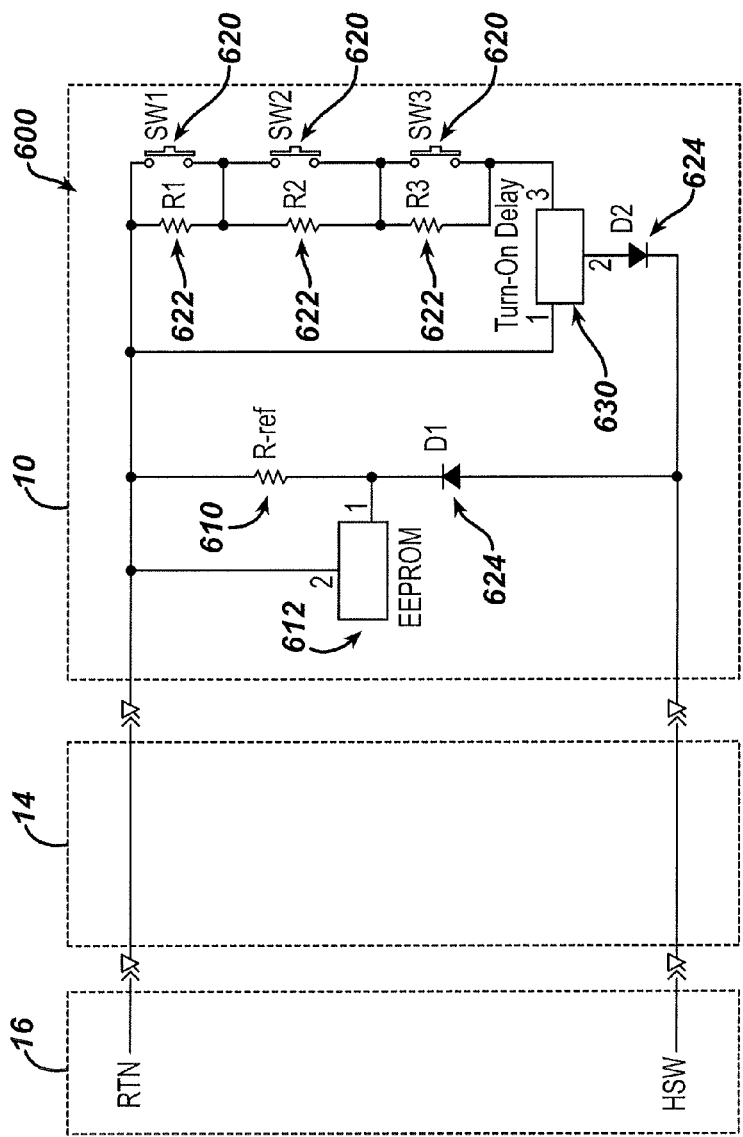
FIG. 17 depicts a schematic view of another exemplary circuit suited for incorporation in the instrument of FIG. 1.

FIG. 17 shows another merely exemplary circuit (600) that may be incorporated into instrument (10) to account for variations in resistance as described above. Circuit (600) is substantially similar to circuit (500) described above, in that circuit (600) includes a reference resistor (610), an EEPROM (612), switches (620), resistors (622), and diodes (624) that are all arranged in a manner similar to the arrangement of reference resistor (510), an EEPROM (512), switches (520), resistors (522), and diodes (524) of circuit (500). Circuit (600) also includes a turn-on delay circuit (630), which may be configured and operable just like turn-on delay circuit (530) described above. However, in this example turn-on delay circuit (630) is inserted at the opposite end of switch (620) ladder. Such positioning of turn-on delay circuit (630) may allow the use of an output stage that employs an n-channel FET or an essentially open-drain integrated circuit (e.g., a Zetex ZSCT1555 low-voltage 555 timer).

Figure 18:
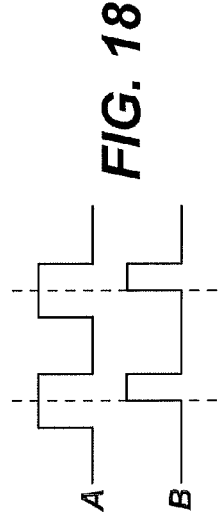
FIG. 18 depicts exemplary output waveforms of the circuits of FIGS. 15-17.

FIG. 18 shows exemplary input and output waveforms of turn-on delay circuits (430, 530, 630). In particular, signal A represents an input signal for turn-on delay circuit (430, 530, 630); while signal B represents an output signal for turn-on delay circuit (430, 530, 630).

Figure 19:
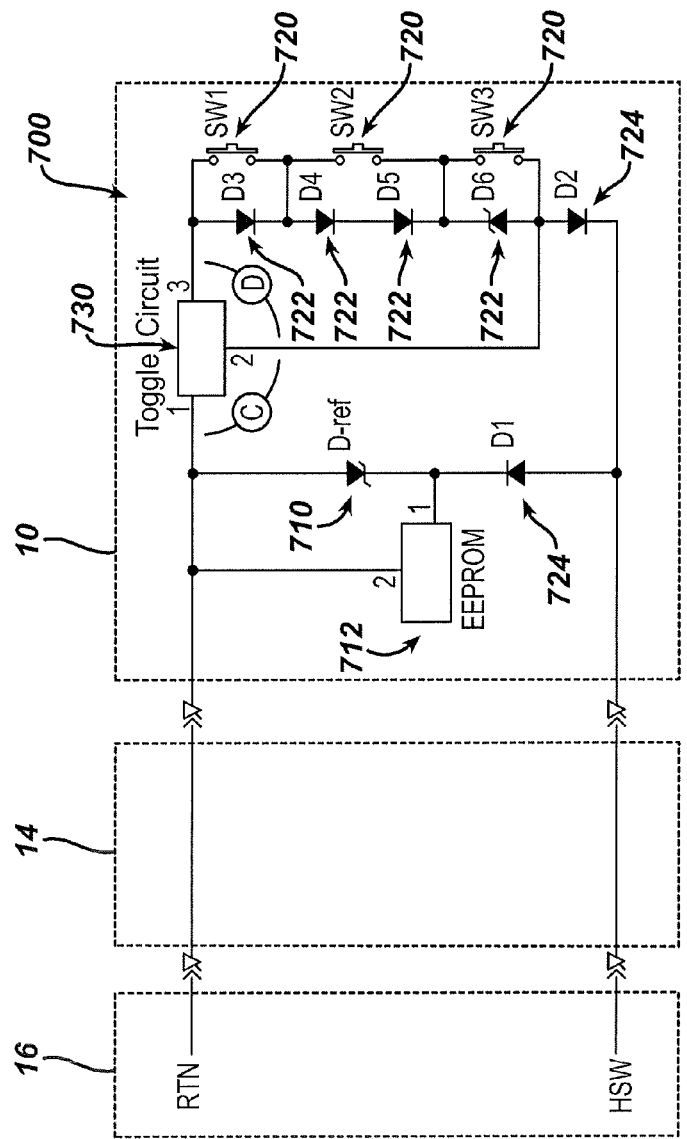
FIG. 19 depicts a schematic view of another exemplary circuit suited for incorporation in the instrument of FIG. 1.
Figure 20:
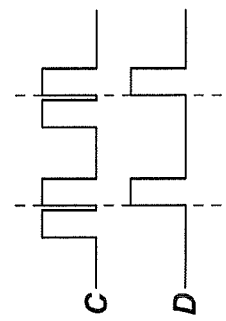
FIG. 20 depicts exemplary output waveforms of the circuit of FIG. 19.

FIG. 19 shows another merely exemplary circuit (700) that may be incorporated into instrument (10) to account for variations in resistance as described above. Circuit (700) is substantially similar to circuit (400) described above, in that circuit (300) includes a reference zener diode (710), an EEPROM (712), switches (720), and diodes (722, 724) that are all arranged in a manner similar to the arrangement of zener diode (410), EEPROM (412), switches (420), and diodes (422, 424) of circuit (400). Unlike circuit (400), circuit (700) of this example further includes a toggle circuit (730) in place of turn-on delay circuit (430). Toggle circuit (730) of this example is a flip-flop type of circuit that is triggered by a second pulse during the negative half-cycle, and reset by the positive pulse on the positive half-cycle. While not shown, it should be understood that toggle circuit (730) may alternatively be positioned at the opposite end of the switch (720) ladder (e.g., similar to the placement of turn-on delay circuit (630) in circuit (600). FIG. 20 shows exemplary input and output waveforms of toggle circuit (730). In particular, signal C represents an input signal for toggle circuit (730); while signal D represents an output signal for toggle circuit (730).

It should be understood that the circuits (200, 300, 400, 500, 600, 700) described above are merely illustrative examples. Various other suitable components, features, and techniques may be used to alternately switch in a reference feature alone, and then either a switch ladder in parallel with the reference feature, or by itself. It should also be understood that the number of switches (220, 320, 420, 520, 620, 720) may vary; such that more than three switches (220, 320,

420, 520, 620, 720) or less than three switches (220, 320, 420, 520, 620, 720) may be used.

IV. Exemplary Single-Use Features

At least one or more portions of some versions of instrument (10) may be sterilized and reused. For instance, it may be desirable to reclaim and reuse electrical components within handle assembly (20), such as circuits, etc. However, it may be undesirable for other portions of handle assembly (20) to be re-used, such as the outer housing of handle assembly (20), buttons (26), etc. Thus, it may be desirable to configure handle assembly (20) such that some components within handle assembly (20) may be reclaimed and re-used; yet such that other portions of handle assembly (20) may not be reclaimed and re-used. In some settings, at least a portion of instrument (10) may be re-used after instrument (10) has been used in a surgical procedure. In some other settings, at least a portion of instrument (10) may be re-used before instrument (10) even leaves a manufacturing facility. For instance, if an instrument (10) fails a quality control test, one or more components of the instrument (10) (e.g., those that had no impact on the quality control test failure) may be reclaimed and re-used to build another instrument (10). Several examples of configurations that may be incorporated into handle assembly (20) to provide selective reusability will be described in greater detail below; while still other examples will be apparent to those of ordinary skill in the art in view of the teachings herein.

In some versions of instrument (10), at least part of the circuitry may include a flex circuit that is formed as a laminate. One or more regions of the outer layer of this laminate may be adhered to the housing of handle assembly (20), such that one or more layers are pulled away from the flex circuit when the housing is disassembled during a reclamation process, such that the flex circuit would be damaged. Such pulling away of layers may render the flex circuit inoperable. In some such instances, an entire outer layer of a circuit is adhered to the housing of handle assembly (20). In some other instances, only portions of the circuit near key circuit components are adhered to the housing of handle assembly (20). As another variation, one or more components of the circuit may be adhered to the housing of handle assembly (20), without necessarily adhering the flexible laminate of a flex circuit to the housing of handle assembly (20). In some such versions, the flexible laminate of the flex circuit may be perforated or otherwise weakened, providing a controlled breakage region such that the flex circuit tears away from the adhered circuit component while the adhered circuit component remains with the housing of the handle assembly when the handle assembly portions are pulled apart during an attempted reclamation. As yet another merely illustrative example, one or more regions of a circuit in handle assembly (20) may be sensitive to water, alcohol, or other fluid, such that the circuit is destroyed when such regions come into contact with water, alcohol, or other fluid that may be used during an attempted reclamation. For instance, a circuit laminate may be configured to delaminate upon contact with water, alcohol, or other fluid.

Figure 21:
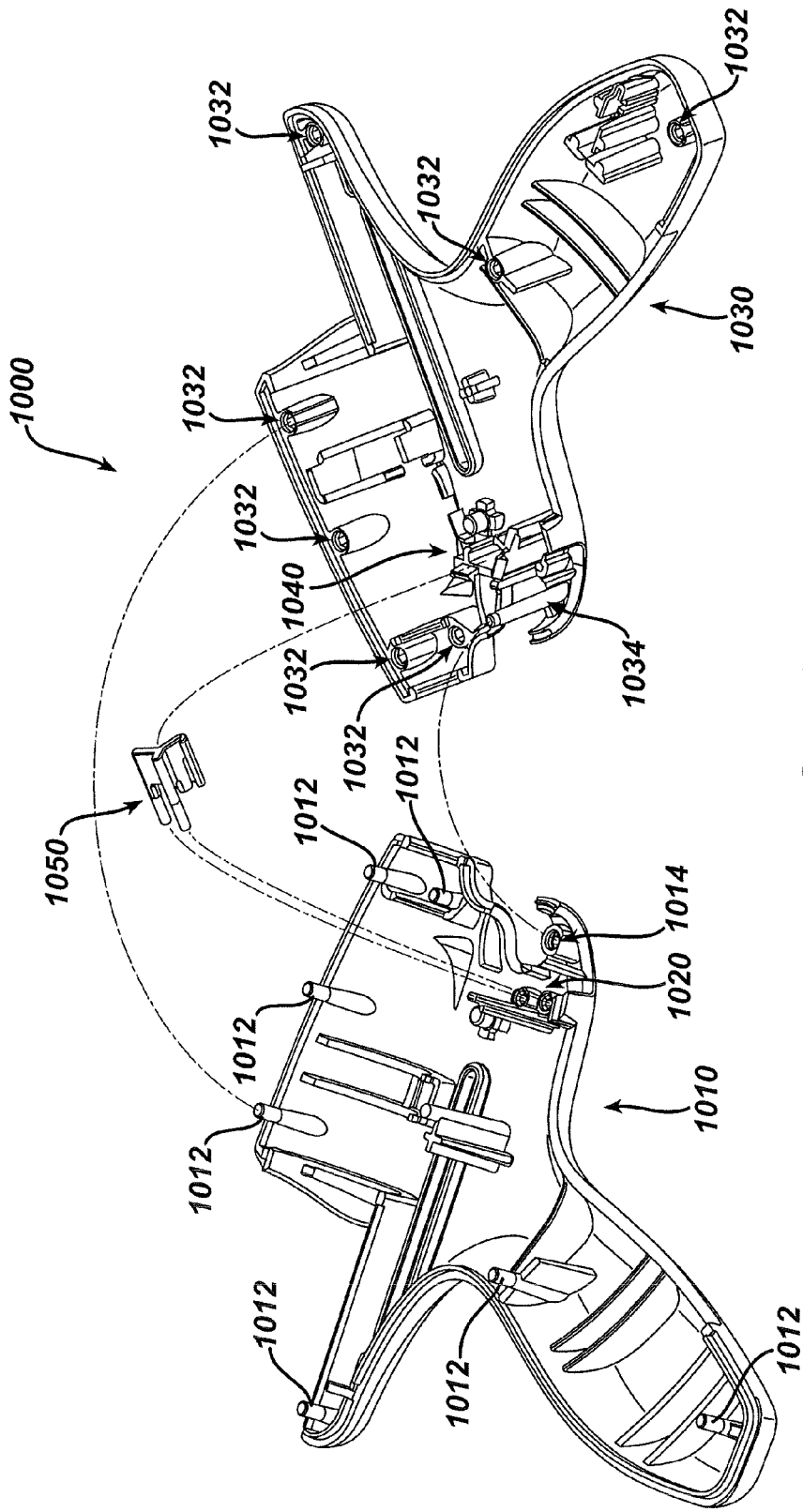
FIG. 21 depicts an exploded perspective view of exemplary housing components that may be incorporated into the instrument of FIG. 1.
Figure 22:
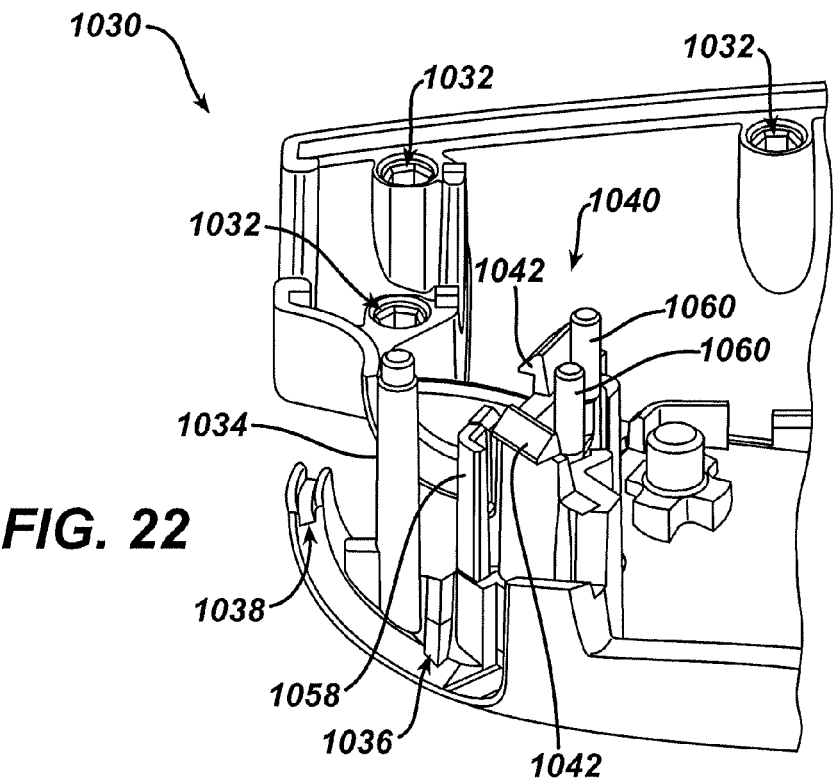
FIG. 22 depicts a partial perspective view of a first housing of the housing components of FIG. 21.
Figure 23:
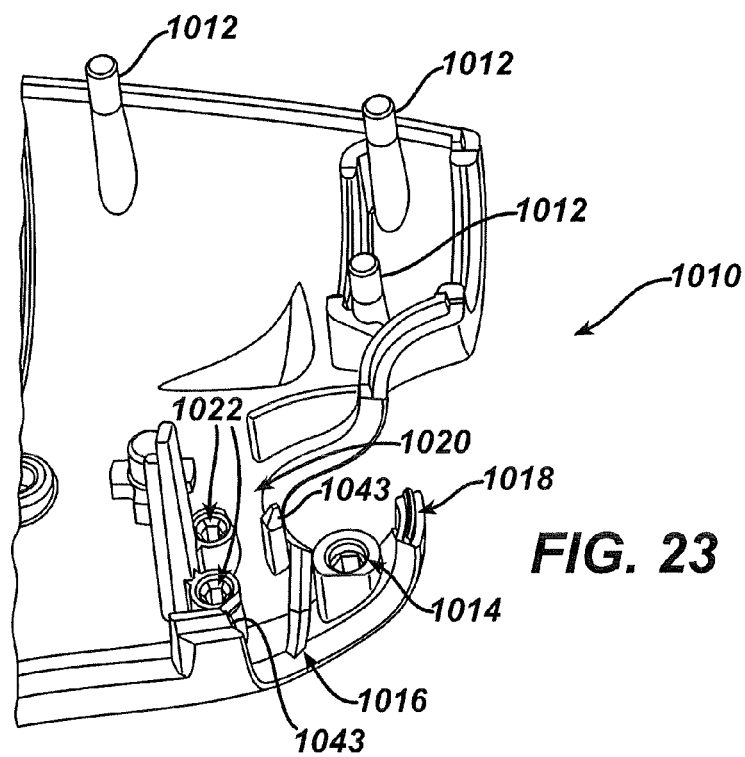
FIG. 23 depicts a partial perspective view of a second housing of the housing components of FIG. 21.

FIGS. 21-25 show an exemplary handle housing assembly (1000) that may be incorporated into instrument (10). Assembly (1000) of this example includes a first housing member (1010), a second housing member (1030), and a retention member (1050). As best seen in FIG. 21, housing member (1010) includes a plurality of posts (1012) and a socket (1014). As also best seen in FIG. 21, housing member (1030) includes a plurality of sockets (1032) and a post (1034). Posts (1012, 1034) are configured for insertion into corresponding sockets (1014, 1032) to secure housing members (1010, 1030) together. By way of example only, posts (1012, 1034) may be press-fit into corresponding sockets (1014, 1032), may be secured in sockets (1014, 1032) using ultrasonic welding, may be heat-staked in sockets (1014, 1032), may be adhered in sockets (1014, 1032) using adhesive, and/or may be otherwise secured relative to sockets (1014, 1032). As best seen in FIGS. 22-23, housing members (1010, 1030) also include complementary tongue-and-groove features (1018, 1038). In some other versions, tongue-and-groove features (1018, 1038) are replaced with complementary shiplap features or some other kind of structures. Tongue-and-groove features (1018, 1038) may be secured together through interference fitting, ultrasonic welding, heat-staking, adhesive, etc.

As also best seen in FIGS. 22-23, housing members (1010, 1030) each include a weakened strip (1016, 1036) in the form of a v-shaped cutout. Weakened strips (1016, 1036) provide reduced wall thicknesses that promote breakage along weakened strips (1016, 1036) when housing members (1010, 1030) are pulled apart. In other words, when a person attempts to separate joined housing members (1010, 1030) by pulling joined housing members (1010, 1030) apart, one or both of housing members (1010, 1030) may break its respective weakened strip (1016, 1036). Thus, a fragment of one housing member (1010, 1030) may remain joined to the other housing member (1010, 1030) while the rest of the fragmented housing member (1010, 1030) may be free from the other housing member (1010, 1030). This breakage/fragmentation may prevent re-use of both housing members (1010, 1030). The smaller fragment of the broken housing member (1010, 1030) may remain joined to the other housing member (1010, 1030) due to the secure relationship between tongue-and-groove features (1018, 1038), between socket (1014) and post (1034), and/or otherwise. Other suitable ways in which controlled breakage may be provided in housing members (1010, 1030) will be apparent to those of ordinary skill in the art in view of the teachings herein.

Figure 24:
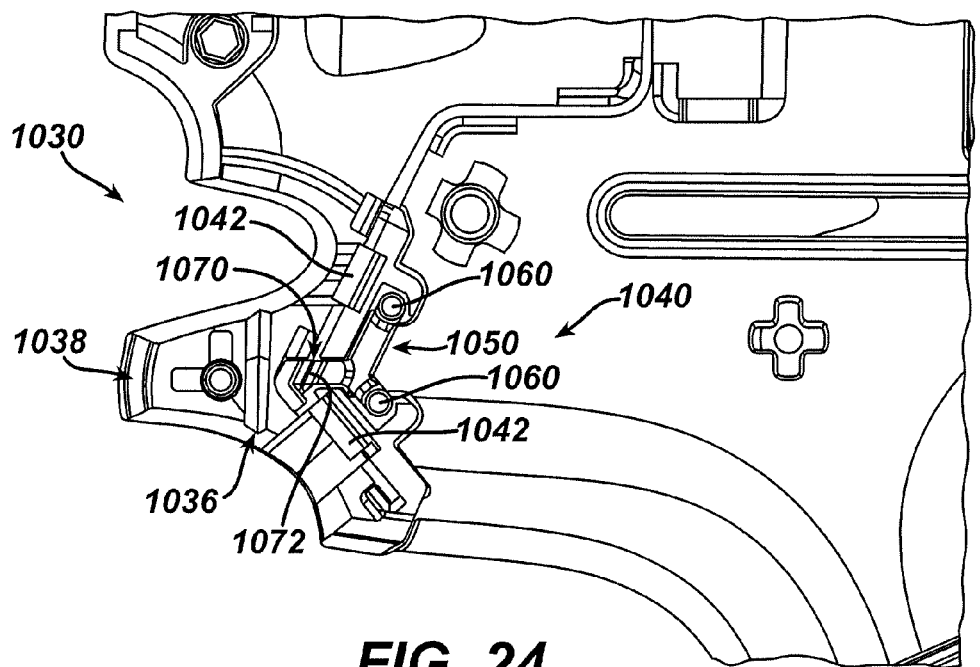
FIG. 24 depicts a partial side elevational view of the first housing of FIG. 22 coupled with an exemplary retention feature.
Figure 25:
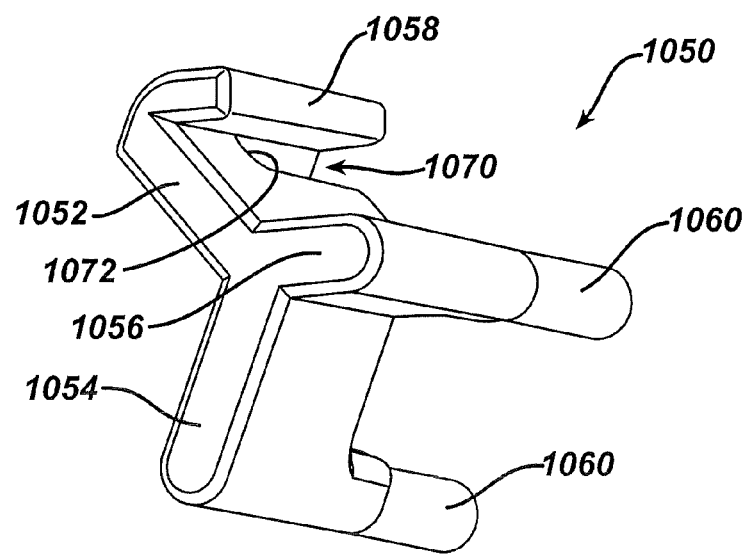
FIG. 25 depicts a perspective view of the retention feature of FIG. 24.

As best seen in FIG. 25, retention member (1050) of the present example generally has a "Y" shape, with a first branch (1052), a second branch (1054), and a third branch (1056). First branch (1052) includes a bent section (1058) and a recess (1070) that terminates at an edge (1072). Second and third branches (1054, 1056) each have respective posts (1060). As best seen in FIGS. 21 and 24, retention member (1050) is configured to fit in retention member features (1020, 1040) of housing members (1010, 1030). As shown in FIG. 23, retention member feature (1020) of housing member (1010) comprises a pair of sockets (1022) that have a hexagonal profile. Sockets (1022) are configured to receive posts (1060) through an interference fitting. Of course, sockets (1022) may have any other suitable configuration; and ultrasonic welding, heat-staking, adhesive, etc., may also be used to secure posts (1060) in sockets (1022). As shown in FIGS. 22 and 24, retention member feature (1040) of housing member (1030) comprises a pair of snap latch members (1042). Retention member (1050) may be slid into position behind snap latch members (1042), such that snap latch members (1042) may assist in maintaining the positioning of retention member (1050) relative to housing member (1030). As shown, bent section (1058) of retention member (1050) passes between and in front of snap latch members (1042) when branches (1054, 1056) are positioned behind snap latch members (1042).

In the present example, one or more switch assemblies (not shown) are positioned behind buttons (26), and include switching circuitry that is responsive to actuation of buttons (26). Recess (1070) is sized to receive a portion of such a switch assembly. In particular, a switch assembly may be slid between bent section (1058) of first branch (1052) and snap latch members (1042), with the switch assembly being received in recess (1070). Snap latch members (1042) assist in holding the switch assembly in position relative to housing member (1030). A pair of ribs (1043) defined in housing member (1010) also hold the switch assembly against housing member (1030). Thus, one outer edge of the switch assembly is retained by snap latch members (1042) while the opposite outer edge of the switch assembly, which is seated in recess (1070), is retained by retention member (1050). Since retention member (1050) is secured to housing member (1010), it should be understood that retention member (1050) and snap latch members (1042) will exert opposing forces on the outer edges of the switch assembly as housing members (1010, 1030) are pulled apart. These opposing surfaces on the switch assembly may sever/break the switch assembly (e.g., by shearing) or otherwise render it inoperable. Thus, if a person attempts to disassembly handle assembly (1000) by pulling housing members (1010, 1030) apart, doing so will also destroy the switch assembly that is located behind buttons (26). The switch assembly may comprise any suitable components such as rigid circuit boards, flexible circuits, wires, conventional switches, etc. In some instances, edge (1072) is sharp to facilitate severing of the switch assembly.

While snap latch members (1042) retain the switch assembly relative to housing member (1030) in the present example, it should be understood that a switch assembly may be otherwise retained relative to housing member (1030). For instance, at least part of the switch assembly may be welded to housing member (1030) (e.g., using spin welding, ultrasonic welding, heat-staking, adhesives, etc.). As another merely illustrative example, a secondary retention feature may be overlaid about recess (1070) of retention member (1050). As yet another merely illustrative example, the switch assembly may be adhered to housing member (1030). Other suitable ways in which a switch assembly may be secured will be apparent to those of ordinary skill in the art in view of the teachings herein.

Figure 26:
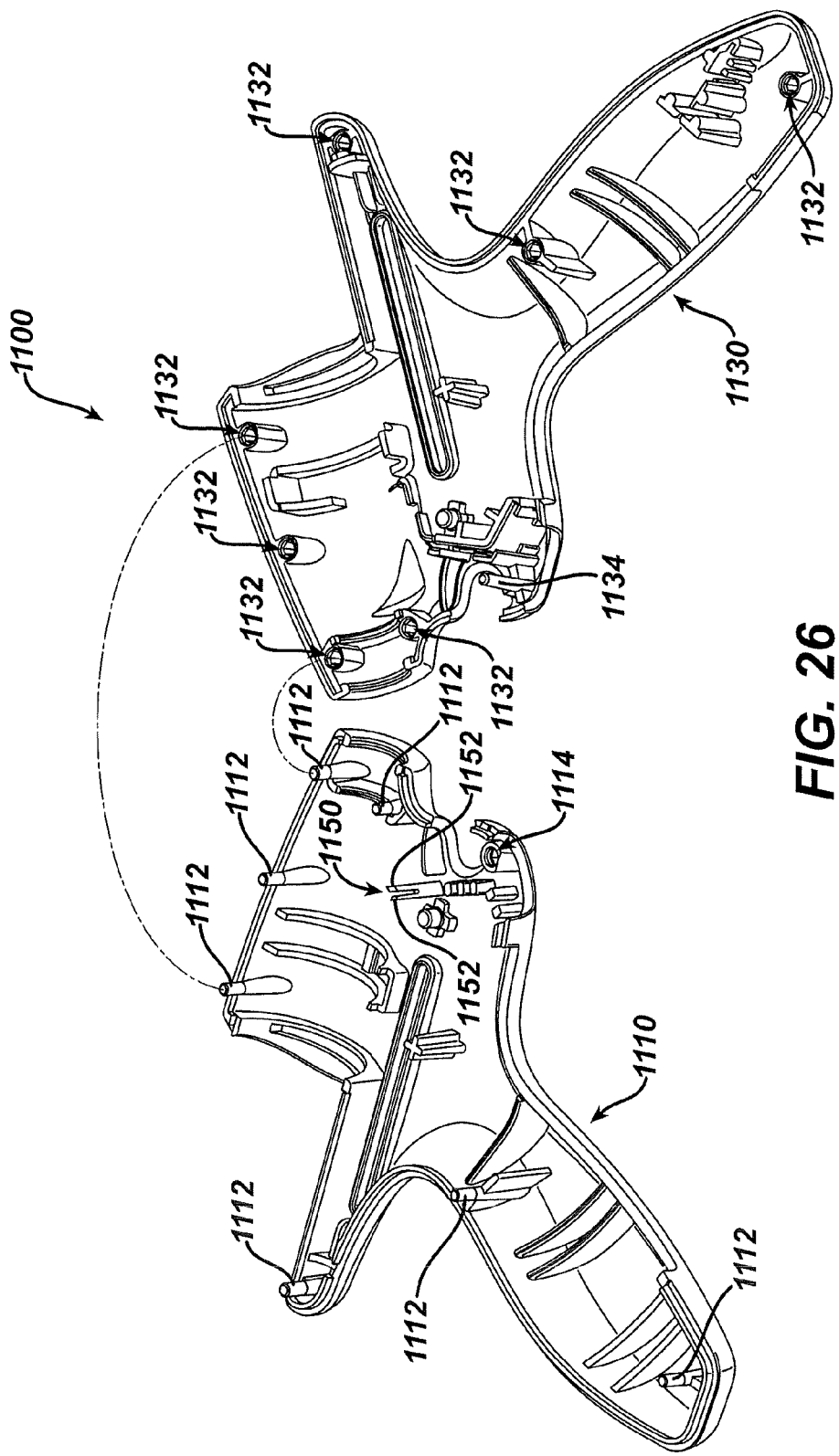
FIG. 26 depicts an exploded perspective view of exemplary alternative housing components that may be incorporated into the instrument of FIG. 1.

FIG. 26 shows another exemplary handle housing assembly (1100) that may be incorporated into instrument (10). Assembly (1100) of this example includes a first housing member (1110) and a second housing member (1130). Housing member (1110) includes a plurality of posts (1112) and a socket (1114). Housing member (1130) includes a plurality of sockets (1132) and a post (1134). Posts (1112, 1134) are configured for insertion into corresponding sockets (1114, 1132) to secure housing members (1110, 1130) together. By way of example only, posts (1112, 1134) may be press-fit into corresponding sockets (1114, 1132), may be secured in sockets (1114, 1132) using ultrasonic welding, may be heat-staked in sockets (1114, 1132), may be adhered in sockets (1114, 1132) using adhesive, and/or may be otherwise secured relative to sockets (1114, 1132).

Housing member (1110) includes an integral retention feature (1150) that comprises a pair of prongs (1152). Prongs (1152) define a gap configured to receive a portion of a switch assembly, which may include switching circuitry that is responsive to actuation of buttons (26). An adhesive may be used to adhere the switch assembly to prongs (1152). In instances where housing assembly (1100) is disassembled, the switch assembly may be retained in retention feature (1150). It should be understood that, due to the adhesion of the switch assembly in retention feature (1150), a person who is assembling several housing assemblies (1100) may be able to quickly identify housing assembly (1100) as one that had already been assembled and perhaps later disassembled. This may prompt the person to discard the housing assembly (1100) as scrap. In addition, an adhesive may be used to adhere the switch assembly to an adjacent region of housing member (1130). Thus, when housing assembly (1100) is disassembled by pulling housing members (1110, 1130) apart, the switch assembly may be ripped apart and thereby rendered inoperable. Again, if two torn-apart switch assembly fragments remain adhered to each housing member (1110, 1130), a person who is assembling several housing assemblies (1100) may be able to quickly identify housing assembly (1100) as one that had already been assembled and later disassembled.

Figure 27:
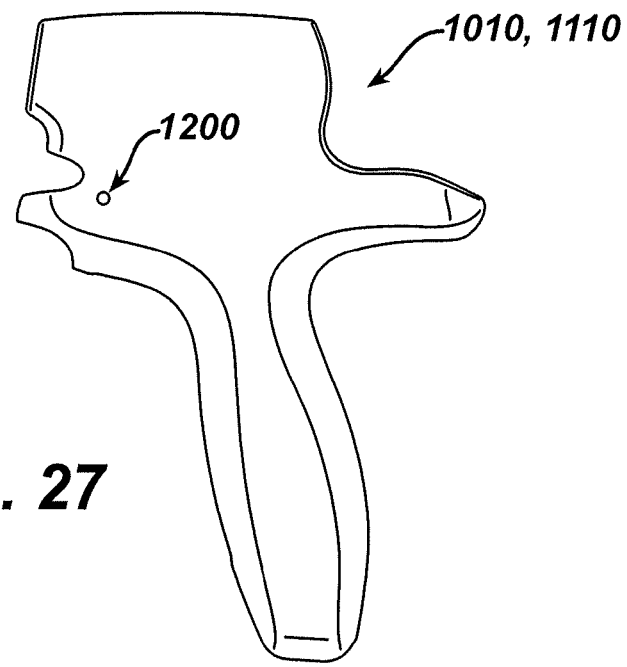
FIG. 27 depicts a side elevational view of a first exemplary housing component from the instrument of FIG. 1, with a hole formed to facilitate separation from a second housing component.
Figure 28:
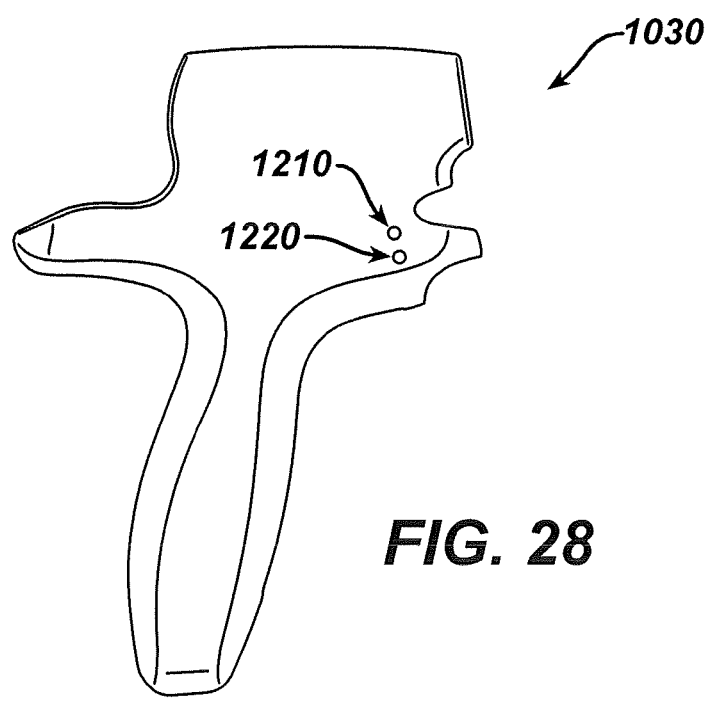
FIG. 28 depicts a side elevational view of a second exemplary housing component from the instrument of FIG. 1, with a hole formed to facilitate separation from a first housing component.

In some instances, it may be desirable to carefully disassemble a handle assembly (20) while minimizing destruction of handle assembly (20). For instance, this may be done to salvage at least a portion of handle assembly (20) and/or something within handle assembly (20). With some versions of handle assembly (20), this may be accomplished by carefully drilling one or more holes in handle assembly (20). For instance, FIG. 27 shows an example where a hole (1200) may be drilled in a housing member (1010, 1110) at a location corresponding to post (1034, 1134) and socket (1014, 1114), thereby effectively decoupling post (1034, 1134) and socket (1014, 1114). FIG. 28 shows an example where holes (1210, 1220) are drilled in a housing member (1030) at locations corresponding to posts (1060) and sockets (1022), thereby effectively decoupling posts (1060) and sockets (1022). Of course, housing members (1010, 1030, 1110, 1130) may be drilled in numerous other locations, including those associated with posts (1012, 1112) and sockets (1032, 1132). The drilled holes may facilitate separation of housing member (1010, 1110) from housing member (1030, 1130) with minimal force, may substantially maintain structural integrity of housing members (1010, 1110, 1030, 1130), and/or may minimize damage to components within housing members (1010, 1110, 1030, 1130). In instances where a drilled housing member (1010, 1110, 1030, 1130) may be re-used, the drilled hole may be filled in, covered, or otherwise dealt with.

Figure 29:
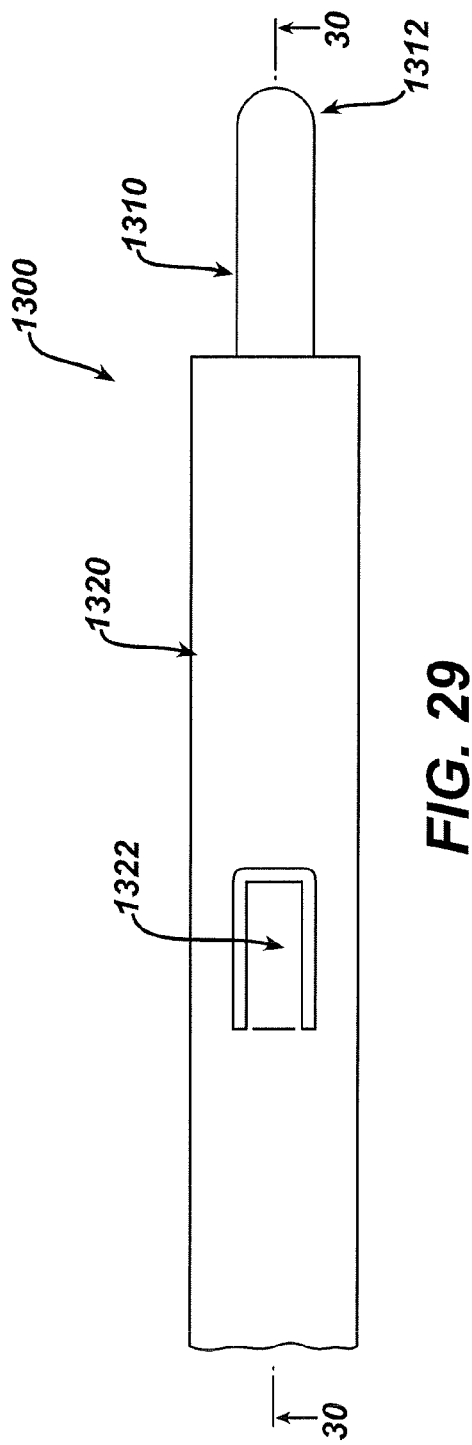
FIG. 29 depicts a top plan view of an exemplary ultrasonic blade assembly that may be incorporated into the instrument of FIG. 1.
Figure 30:
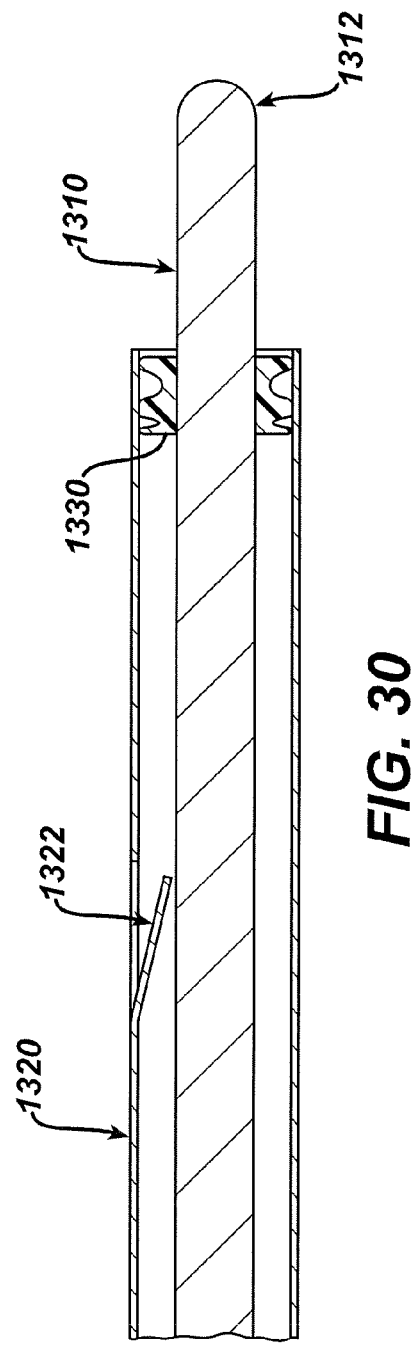
FIG. 30 depicts a cross-sectional side view of the blade assembly of FIG. 29, taken along line 30-30 of FIG. 29.

FIGS. 29-30 show an exemplary ultrasonic blade assembly (1300) comprising an ultrasonic blade (1310) disposed in a tube (1320). Ultrasonic blade (1310) is positioned such that a distal end (1312) of blade (1310) is exposed relative to tube (1320). Tube (1320) has an inner diameter that is substantially greater than the outer diameter of blade (1310), such that a cylindraceous gap is defined between the inner diameter of tube (1320) and the outer diameter of blade (1310). An annular overmold (1330) is positioned about the exterior of blade (1310) to support blade (1310) relative to tube (1320). By way of example only, overmold (1330) may be formed of a plastic material or an elastomeric material. Overmold (1330) may be located at a longitudinal position corresponding to a node associated with resonant ultrasonic vibrations communicated through blade (1310). The positioning and/or properties of overmold (1330) provide substantial acoustic isolation of tube (1320) relative to blade (1310). While one overmold (1330) is shown, it should be understood that several overmolds may be used. It should also be understood that features other than overmold (1330) may be used. By way of example only, one or more o-rings located at nodes may be used instead of overmold (1330).

Tube (1320) includes a distally directed tab (1322) formed by a "U"-shaped cut in tube (1320). As best seen in FIG. 30, tab (1322) is directed inwardly and distally within tube (1320). In the present example, tab (1322) does not contact ultrasonic blade (1310). In some other versions, tab (1322) contacts ultrasonic blade (1310) at a node associated with resonant ultrasonic vibrations communicated through blade (1320). Tab (1322) is resilient such that tab (1322) deflects out of the way when blade (1310) and overmold (1330) are inserted distally through tube (1320) during assembly of ultrasonic blade assembly (1300); yet tab (1322) returns back to the position shown in FIG. 30 after overmold (1330) clears tab (1322). However, if blade (1310) and overmold (1330) are retracted proximally through tube (1320) during disassembly of ultrasonic blade assembly (1300), tab (1322) will tear through overmold (1330) or otherwise destroy overmold (1330). To the extent that someone attempts to later re-use blade (1310) and overmold (1330), the destroyed overmold (1330) would cause the rebuilt ultrasonic blade assembly (1300) to fail a leak test.

Figure 31:
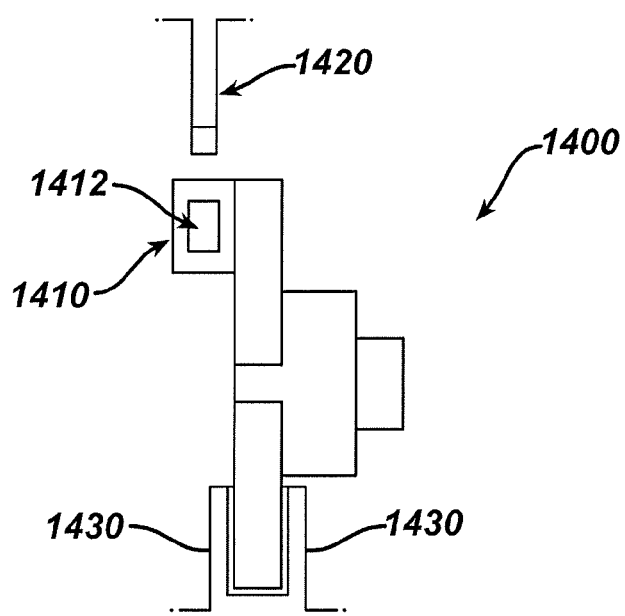
FIG. 31 depicts a top partial view of an exemplary power cable connection assembly, with one housing half of a surgical instrument separated from the connection assembly and another housing half engaged with the connection assembly.
Figure 32:
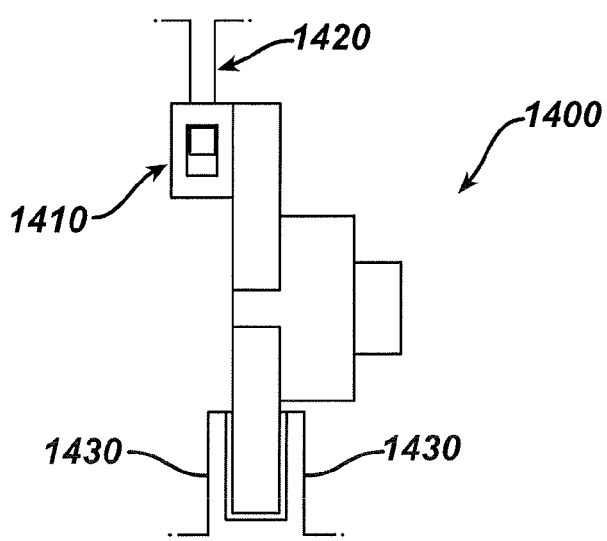
FIG. 32 depicts a top partial view of an exemplary power cable connection assembly, with the housing halves secured to the connection assembly.

In some versions of instrument (10), transducer assembly (12) may be supported within handle assembly (20) by a connector housing that permits transducer assembly (12) to rotate relative to handle assembly (20), about the longitudinal axis defined by transducer assembly (12). FIGS. 31-32 show an example of such a connector housing (1400) along with exemplary features that may be used to couple connector housing (1400) to handle assembly (20). In particular, connector housing (1400) of this example includes a retention boss (1410) that defines an opening (1412). One housing half of the handle includes a retention clip (1420); while another housing half of the handle includes a pair of retention flanges (1430). Retention clip (1420) includes a pair of barbed arms (not shown). The barbed arms are configured to fit through opening (1412) of retention boss (1410) and thereby provide a snap fit between connector housing (1400) and the associated housing half of the handle, as shown in the transition from FIG. 31 to FIG. 32. Flanges (1430) are configured to partially encompass connector housing (1400) and thereby restrict movement of connecting housing (1400) to some degree; yet still permit connector housing (1400) to float within the handle assembly to some degree.

In another example a first clamshell half (not shown) and a second clamshell half (not shown) join together to encompass a connector housing (not shown) that is similar to connector housing (1400) described above. The joined halves may couple with handle assembly (20) through gripper pins, adhesive, ultrasonic welding, some other form of welding, or in any other suitable fashion. The joined halves may or may not move relative to handle assembly (20). However, the joined halves may enable the connector housing to float relative to the joined halves as needed. As another merely illustrative variation, a silicone member may be interposed between the connector housing and handle assembly (20) instead of joined halves. Such a silicone member may substantially retain the connector housing within handle assembly (20) yet still permit some degree of movement (i.e., floating) of the connector housing relative to handle assembly (20). Other suitable ways in which a connector housing may be coupled with a handle assembly will be apparent to those of ordinary skill in the art in view of the teachings herein. These connector housing coupling features may be used in conjunction with any of the features described above to provide a way of recognizing a used switch assembly or shroud.

V. Miscellaneous

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus for operating on tissue, the apparatus comprising:
   (a) a body;
   (b) an ultrasonic transducer operable to convert electrical power into ultrasonic vibrations;
   (c) a shaft extending distally from the body, wherein the shaft defines a longitudinal axis; and
   (d) an end effector at the distal end of the shaft, wherein the end effector comprises an ultrasonic blade in acoustic communication with the ultrasonic transducer, wherein the ultrasonic blade includes a recess region having a plurality of recesses and extending a length from a proximal end to a distal tip, wherein the recess region further includes a concave transition and a tapered region, wherein the concave transition of the recess region is distally positioned relative to the proximal end, wherein the tapered region of the recess region is distally positioned relative to the concave transition and tapered such that a cross-sectional area of the tapered region continuously decreases along the length of the tapered region toward the distal tip,
   wherein the recesses in the concave transition include a first recess and a second recess, wherein the first recess has a first arcuate section defined by a first radius swept along a first plane passing through the longitudinal axis of the shaft, wherein the longitudinal axis of the shaft extends along the first plane, wherein the second recess includes a second arcuate section defined by a second radius swept along the first plane, and
   wherein the recesses in the tapered region further include a third arcuate section defined at least partially by a third radius swept along a second plane, wherein the second plane is parallel to the first plane, wherein the second plane is offset from the first plane such that the longitudinal axis of the shaft does not extend along the second plane.

2. The apparatus of claim 1, wherein the ultrasonic blade is curved such that a central longitudinal axis of the ultrasonic blade extends along a curved path.

3. The apparatus of claim 2, wherein the distal tip is laterally offset relative to the longitudinal axis defined by the shaft.

4. The apparatus of claim 1, wherein the first and second arcuate sections are on opposite sides of the ultrasonic blade.

5. The apparatus of claim 4, wherein the ultrasonic blade is curved such that a central longitudinal axis of the ultrasonic blade extends along a curved path, wherein the first arcuate section is positioned on an inside region of the curve of the ultrasonic blade, wherein the second arcuate section is positioned on an outside region of the curve of the ultrasonic blade.

6. The apparatus of claim 1, wherein the ultrasonic blade extends along a central longitudinal axis and the third arcuate section is further defined in part by a fourth radius swept along a third plane, wherein the central longitudinal axis perpendicularly intersects the third plane and the third plane is perpendicular to the first and second planes, and wherein the third arcuate section in the third plane is concave to define a concave surface.

7. The apparatus of claim 6, wherein the central longitudinal axis extends along a fourth plane that is perpendicular to the first plane and perpendicular to the third plane, wherein the intersection of the ultrasonic blade and the third plane defines a blade cross-section bisected by the fourth plane into a first blade portion and a second blade portion, and wherein the first blade portion of the blade cross-section includes a first convex surface intersecting the concave surface at a back-cutting edge.

8. The apparatus of claim 7, wherein the second blade portion of the blade cross-section includes a second convex surface positioned opposite from each of the first convex and concave surfaces of the first blade portion.

9. The apparatus of claim 1, wherein the first and third arcuate sections share a common edge.

10. The apparatus of claim 1, wherein the first arcuate section proximally terminates at a first position along the length of the ultrasonic blade, wherein the third arcuate section proximally terminates at a second position along the length of the ultrasonic blade, wherein the second position is proximal relative to the first position.

11. The apparatus of claim 1, wherein part of the third arcuate section terminates at a back-cutting edge.

12. The apparatus of claim 1, wherein the ultrasonic blade further comprises a balance feature formed by a concave cut extending circumferentially about the ultrasonic blade.

13. The apparatus of claim 1, wherein the first radius is between about 0.2 inches and about 0.25 inches, wherein the second radius is between about 0.25 inches and about 0.275 inches, and wherein the first radius and the second radius are thereby configured to balance the ultrasonic blade for operation via the ultrasonic transducer.

14. The apparatus of claim 13, wherein the third radius is between approximately 1.390 inches and approximately 1.500 inches and thereby configured to further balance the ultrasonic blade for operation via the ultrasonic transducer.

15. The apparatus of claim 1, wherein the ultrasonic blade extends along a central longitudinal axis and has a pair of lateral portions on opposing respective laterals sides of the central longitudinal axis, and wherein each of the pair of lateral portions tapers inward toward the central longitudinal axis along the length of the tapered region.

16. The apparatus of claim 1, wherein the first and second recesses in the concave transition are positioned laterally opposite from each other.

17. An apparatus, comprising:
   (a) a surgical instrument, wherein the surgical instrument includes one or more variable voltage drop features configured to provide a variable voltage drop during operation of the surgical instrument;
   (b) a power source in communication with the surgical instrument, wherein the power source is operable to provide power to the surgical instrument, wherein the power source is configured to generate an interrogation signal at a cycle, wherein the cycle includes a first cycle portion and a second cycle portion; and
   (c) a reference circuit in communication with the surgical instrument, wherein the reference circuit is further in communication with the power source, wherein the reference circuit includes one or more predetermined voltage drop features configured to provide a predetermined voltage drop during operation of the surgical instrument;

wherein the one or more variable voltage drop features and the reference circuit are electrically connected with the power source in parallel, wherein the power source is configured to read the one or more predetermined voltage drop features of the reference circuit with the first cycle portion of the interrogation signal, wherein the power source is configured to read the one or more variable voltage drop features with the second cycle portion of the interrogation signal, wherein the power source is operable to subtract out a voltage drop from the one or more variable voltage drop features based on a voltage drop from the one or more predetermined voltage drop features during operation of the surgical instrument.

18. The apparatus of claim 17 wherein the reference circuit further comprises a turn-on delay circuit electrically connected between the one or more predetermined voltage drop features and the one or more variable voltage drop features, wherein the turn-on delay circuit is configured to cycle such that the interrogation signal interrogates only the one or more predetermined voltage drop features of the reference circuit during a first portion of the first cycle portion, and wherein the turn-on delay circuit is configured to further cycle such that the interrogation signal interrogates only the one or more variable voltage drop features during a second portion of the first cycle portion.

19. The apparatus of claim 18, wherein the reference circuit further includes an EEPROM electrically connected to the one or more predetermined voltage drop features.

20. A method of operating a surgical instrument, the surgical instrument including one or more variable voltage drop features, a power source, and a reference circuit having one or more predetermined voltage drop features, wherein the one or more variable voltage drop features are configured to provide a variable voltage drop during operation of the surgical instrument, wherein the power source is in communication with the surgical instrument, wherein the power source is operable to provide power to the surgical instrument, wherein the reference circuit is in communication with the surgical instrument, wherein the reference circuit is further in communication with the power source, wherein the one or more predetermined voltage drop features is configured to provide a predetermined voltage drop during operation of the surgical instrument, and wherein the one or more variable voltage drop features and the reference circuit are electrically connected with the power source in parallel, the method comprising:

(a) generating an interrogation signal at a cycle with the power source, wherein the cycle includes a first cycle portion and a second cycle portion;

(b) reading the one or more predetermined voltage drop features of the reference circuit with the first cycle portion of the interrogation signal;

(c) reading the one or more variable voltage drop features with the second cycle portion of the interrogation signal;

(d) detecting a first voltage drop from the surgical instrument, wherein the first voltage drop results from activation of a switch in the surgical instrument, wherein the value of the first voltage drop is unknown;

(e) detecting a second voltage drop from the surgical instrument, wherein the second voltage drop is caused by the reference circuit providing the predetermined voltage drop such that the value of the second voltage drop is the predetermined voltage drop, wherein the act of detecting the second voltage drop is performed in close time proximity to the act of detecting the first voltage drop; and (f) providing power to the surgical instrument, wherein the act of providing power to the surgical instrument comprises subtracting out the first voltage drop based on the second voltage drop.

\* \* \* \* \*